United States Patent [19]
Casci et al.

[11] Patent Number: 5,464,799
[45] Date of Patent: Nov. 7, 1995

[54] ZEOLITE NU-85 CATALYST

[75] Inventors: John L. Casci, Cleveland; Mervyn D. Shannon, Cheshire; Ivan J. S. Lake, Cleveland, all of England

[73] Assignee: Imperial Chemical Industries PLC, London, England

[21] Appl. No.: 338,142

[22] Filed: Nov. 9, 1994

Related U.S. Application Data

[62] Division of Ser. No. 717,194, Jun. 18, 1991, Pat. No. 5,385,718.

[30]     Foreign Application Priority Data

Jun. 21, 1990 [GB]  United Kingdom .................. 9013859

[51] Int. Cl.⁶ ..................................................... B01J 29/06
[52] U.S. Cl. ................................ 502/65; 502/66; 502/73; 502/74; 502/77
[58] Field of Search ............................. 423/708, 718; 502/65, 66, 73, 74, 77

[56]            References Cited

U.S. PATENT DOCUMENTS

| | | | |
|---|---|---|---|
| 2,950,952 | 8/1960 | Breck et al. | 423/718 |
| 4,086,186 | 4/1978 | Rubin et al. | 502/62 |
| 4,229,424 | 10/1980 | Kokotailo | 502/64 |
| 4,537,754 | 8/1985 | Casci et al. | 423/708 |
| 4,560,542 | 12/1985 | Robson | 423/703 |
| 4,581,212 | 4/1986 | Araya et al. | 423/702 |
| 4,593,138 | 6/1986 | Casci et al. | 585/481 |
| 4,657,750 | 4/1987 | Takatsu et al. | 423/701 |
| 4,705,674 | 11/1987 | Araya et al. | 423/705 |
| 4,741,891 | 5/1988 | Casci et al. | 423/708 |
| 4,743,437 | 5/1988 | Whittam | 423/706 |
| 5,102,641 | 4/1992 | Casci et al. | 423/708 |
| 5,108,579 | 4/1992 | Casci et al. | 208/46 |

FOREIGN PATENT DOCUMENTS

| | | |
|---|---|---|
| 0042226 | 12/1981 | European Pat. Off. . |
| 0377281 | 7/1990 | European Pat. Off. . |

*Primary Examiner*—Mark L. Bell
*Assistant Examiner*—David R. Sample
*Attorney, Agent, or Firm*—Cushman Darby & Cushman

[57]            ABSTRACT

A zeolite, designated NU-85, is an intergrowth of zeolites EU-1 and NU-87. The zeolite is a useful catalyst in a wide variety of hydrocarbon conversion reactions including isomerization and alkylation.

4 Claims, 13 Drawing Sheets

ZEOLITE NU-85 CATALYST

This is division of application Ser. No. 07/717,194, filed Jun. 18, 1991 now U.S. Pat. No. 5,385,718.

FIELD OF THE INVENTION

The present invention relates to a novel crystalline aluminosilicate zeolite designated NU-85, a method of making it and to processes using it as a catalyst.

As the actual structure of crystalline zeolites is often unknown, these materials are usually characterised by their X-ray powder diffraction pattern, molar composition and sorptive and catalytic properties. Techniques such as electron diffraction, transmission electron microscopy and magic-angle spinning nuclear magnetic resonance spectroscopy can, however, be used to give additional information on certain structural features which would not, otherwise, be observed.

Even when the basic framework structure is known, additional information may be required to distinguish between two materials. For example, zeolites X and Y have the same basic topology but differ in the ratio of silica to alumina in the structural framework. Another example is large- and small-port mordenite. These materials have the same X-ray powder diffraction pattern yet have different molecular sieve properties with the large port material's sorption being consistent with the known framework topology. The reason for these differences has been attributed to the fact that the small port material contains structural blockages within its channels, which, it has been reported, can be observed by electron diffraction.

DESCRIPTION OF RELATED ART

Materials which are intergrowths of two zeolites having different topologies also exist. Such materials are not simple mixtures. They are materials in which bands of both zeolites exist within individual crystals. Such intergrowths are new materials since they have properties which can distinguish them from the individual "parent" zeolites. Intergrowths based on erionite/offretite and ZSM-5/ZSM-11 have been described in U.S. Pat. Nos. 4,086,186 and 4,229,424 respectively.

Intergrowths may be characterised by electron diffraction and/or transmission electron microscopy. However, it is possible that the intergrowths may have distinct X-ray powder diffraction patterns which differ from the parent zeolites. For example, U.S. Pat. No. 4,086,186 describes a novel aluminosilicate material, designated ZSM-34, which is an intergrowth of erionite-offretite and which has an X-ray powder diffraction pattern which is different from that of either erionite or offretite. Another example is zeolite T which is the subject of U.S. Pat. No. 2,950,952. This is described in "Zeolite Molecular Sieves", D. W. Breck, published by J. Wiley & Sons, 1974, p81 as a "disordered intergrowth" of offretite and erionite". Like zeolite ZSM-34, the X-ray powder diffraction of this material is different from that of the parent zeolites.

It has now been found that an intergrowth of zeolite EU-1, described in European Patent No 42 226, and zeolite NU-87, described in European Patent Specification No 377 291 can be produced.

The contents of EP-B-42 226 and EP-A-377 291 are incorporated herein by reference. However, for convenience, brief definitions of the zeolites EU-1 and NU-87 are given below.

Zeolite EU-1 has a molar composition expressed by the formula:

0.5 to 1.5 $R_2O:Y_2O_3$: at least 10 $XO_2$:O to 100 $H_2O$ 0.5 to 1.5 $R_2O:Y_2O_3$: at least 10 $XO_2$:O to 100 $H_2O$ X is silicon and/or germanium, Y is one or more of aluminium, iron, gallium or boron, and $H_2O$ is water of hydration additional to water notionally present when R is H and, in its "as-prepared" form, an X-ray diffraction pattern including the lines given in Table A.

TABLE A

Zeolite EU-1 "as prepared"

| d(Angstrom) | Relative Intensity |
|---|---|
| 11.03 | Very Strong |
| 10.10 | Strong |
| 9.72 | Weak |
| 6.84 | Weak |
| 5.86 | Very Weak |
| 4.66 | Very Strong |
| 4.31 | Very Strong |
| 4.00 | Very Strong |
| 3.82 | Strong |
| 3.71 | Strong |
| 3.44 | Medium |
| 3.38 | Medium |
| 3.26 | Strong |
| 3.16 | Very Weak |
| 3.11 | Very Weak |
| 2.96 | Very Weak |
| 2.71 | Very Weak |
| 2.55 | Weak |
| 2.48 | Very Weak |
| 2.42 | Very Weak |
| 2.33 | Very Weak |
| 2.30 | Very Weak |
| 2.13 | Very Weak |

Zeolite NU-87, has a molar composition expressed by the formula: 100 $XO_2$: equal to or less than 10 $Y_2O_3$: equal to or less than 20 $R_{2/n}O$ where R is one or more cations of valency n, X is silicon and/or germanium, Y is one or more of aluminium, iron, gallium, boron, titanium, vanadium, zirconium, molybdenum, arsenic, antimony, chromium and manganese and, in its "as-prepared" form, an X-ray diffraction pattern including the lines given in Table B.

TABLE B

Zeolite NU-87 "as-prepared"

| d(Angstroms) | | Relative Intensity (d) |
|---|---|---|
| 12.52 | ±0.15 | w |
| 11.06 | ±0.15 | s |
| 10.50 | ±0.15 | m |
| 8.31 | ±0.15 | w |
| 6.81 | ±0.12 | w |
| 4.62 | ±0.10 | m–s |
| (a) 4.39 (Sh) | ±0.10 | m–s |
| 4.31 | ±0.10 | vs |
| 4.16 | ±0.10 | m |
| 3.98 | ±0.08 | s–vs |
| (b) 3.92 (Sh) | ±0.08 | s |
| 3.83 | ±0.08 | w–m |
| 3.70 | ±0.07 | m–s |
| 3.61 | ±0.07 | w |
| 3.41 | ±0.07 | m–s |
| (c) 3.37 (Sh) | ±0.07 | m |

TABLE B-continued

Zeolite NU-87 "as-prepared"

| d(Angstroms) | | Relative Intensity (d) |
|---|---|---|
| 3.26 | ±0.06 | s–vs |
| 3.15 | ±0.06 | w |
| 3.08 | ±0.06 | w |
| 2.89 | ±0.05 | w–m |
| 2.52 | ±0.04 | w–m |

(Sh) denotes that the peak occurs as a shoulder on a more intense peak
(a) occurs on the low angle side of the peak at about 4.31Å
(b) occurs on the high angle side of the peak at about 3.98Å
(c) occurs on the high angle side of the peak at about 3.41Å.
(d) Based on a relative intensity scale in which the strongest line in the X-ray pattern is assigned a value of 100:
weak (w) is less than 20
medium (m) is between 20 and 40
strong (s) is greater than 40 but less than 60
very strong (vs) is greater than 60.

As described in EP-B-42 226, zeolite EU-1 is preferably prepared from a reaction mixture containing:

$$SiO_2—Al_2O_3—Na_2O—Q—H_2O$$

where Q is a polymethylene alpha omega-diammonium cation, and is preferably hexamethonium-hexane-1,6-bis (trimethylammonium) ie $$[(CH_3)_3N(CH_2)_6N(CH_3)_3]^{2+}$$

The mixture is usually reacted a temperature between 85 and 250° C.

As described in EP-A-377 291, zeolite NU-87 is preferably prepared from a reaction mixture containing:

$$SiO_2—Al_2O_3—Na_2O—Q—H_2O$$

where Q is most preferably $$[(CH_3)_3N(CH_2)_{10}N(CH_3)_3]^{2+}$$

The mixture is usually reacted a temperature between 85° and 250° C.

Surprisingly, we have now found that certain combinations of reaction mixture composition and temperature produce a novel and useful material, designated zeolite NU-85, which we have identified as an intergrowth of zeolites EU-1 and NU-87.

According to the present invention, zeolite NU-85 comprises crystals containing discreet bands the structures of which are individually characteristic of the structures of zeolite EU-1 and zeolite NU-87, said bands exhibiting substantial crystal lattice continuity therebetween.

According to a further aspect the invention provides a zeolite, designated zeolite NU-85, having a composition expressed on an anhydrous basis, in terms of mole ratios of oxides, by the formula:

$100XO_2$: less than or equal to $10Y_2O_3$: less than or equal to $20R_{2/n}O$ where R is one or more cations of valency n, X is silicon and/or germanium, Y is one or more of aluminium, iron, gallium, boron, titanium, vanadium, zirconium, molybdenum, arsenic, antimony, chromium and manganese and having, in its as prepared form lattice images which, when orientated to show the 20.2±0.2 Angstrom fringes of zeolite EU-1 exhibit intergrown 12.5±0.2 Angstrom fringes together with said 20.2±0.2 Angstrom fringes and/or an X-ray diffraction pattern including the lines shown in Table 1.

The invention also provides zeolite NU-85 in its hydrogen form, produced by calcination and/or ion exchange as described herein.

DESCRIPTION OF PREFERRED EMBODIMENTS

Figure 1:
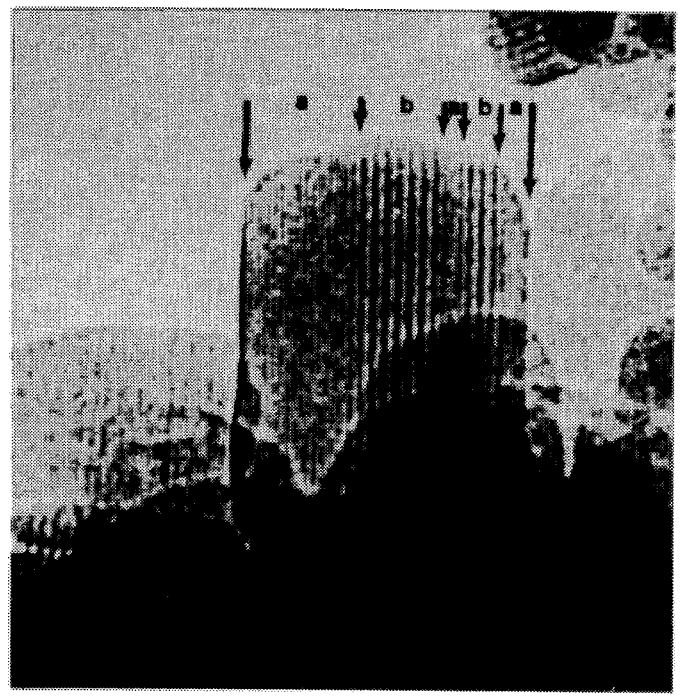
FIG. 1 is a micrograph showing crystals of the zeolite NU-85 prepared according to Example 9.

By "zeolite NU-85" we mean a family of materials the compositions of which can be equated to varying proportions of the two parent zeolites, EU-1 and NU-87. The result of this is that the lines in the X-ray powder diffraction patterns of different samples of zeolite NU-85 may have different intensities. Without being bound by theory, it is believed that the lower the intensity of the XRD (X-ray diffraction) line at 3.8 Å (23.5 degrees two-theta) compared to the line at 3.7 Å (24 degrees two-theta) the greater the proportion of zeolite NU-87 in the intergrowth crystal. It is believed that this relationship will apply to zeolite NU-85 containing up to at least 50% zeolite NU-87 in the intergrowth crystal.

TABLE 1

Zeolite NU-85 as-prepared

| d(Angstroms) | | Relative Intensity* |
|---|---|---|
| 11.15 | ±0.20 | m |
| 10.30 | ±0.20 | w(a) |
| 6.89 | ±0.12 | w |
| 4.66 | ±0.10 | m |
| 4.31 | ±0.10 | vs |
| 4.00 | ±0.08 | s–vs |
| 3.86 | ±0.08 | w–m |
| 3.71 | ±0.07 | m(b) |

TABLE 1-continued

Zeolite NU-85 as-prepared

| d(Angstroms) | Relative Intensity* |
|---|---|
| 3.42 ±0.06 | w–m |
| 3.37 ±0.06 | w–m(c) |
| 3.26 ±0.06 | s–vs |
| 3.16 ±0.06 | w |
| 3.10 ±0.06 | w |
| 2.96 ±0.05 | w |
| 2.71 ±0.05 | w |

*Based on a relative intensity scale in which the strongest line in the X-ray pattern is assigned a value of 100:
w (weak) is less than 20
m (medium) is between 20 and 40
s (strong) is greater than 40 and less than 60
vs (very strong) is greater than 60

It has to be noted, and as will be appreciated by those skilled in the art, the data given in Table 1 is data obtained from a relatively pure sample of material. When the zeolite NU-85 is relatively pure, the following relationships (a), (b) and (c) as identified in Table 1 apply:

a) The ratio of the intensities (rounded to one decimal place) of the line at 10.30 Å to the line at 11.15 Å is not more than 0.5.

b) The ratio of the intensities (rounded to one decimal place) of the line at 3.86 Å to the line at 3.71 Å is not more than 1.0.

c) The ratio of the intensities (rounded to one decimal place) of the line at 3.37 Å to the line at 3.42 Å is not more than 1.0.

In less pure samples, the relationships (a) and (c) may not always be present. However, the X-ray diffraction pattern of zeolite NU-85 will show relationship (b) above, that is the ratio of the intensities of the line at 3.86 Å to the line at 3.71 Å is not more than 1.0. A sample of zeolite NU-85 will preferably also show relationship (a) above in its XRD, that is the ratio of the intensities of the line at 10.30 Å to the line at 11.15 Å is not more than 0.5; and, in particular, will most preferably also show relationship (c) above, that is the ratio of the intensities of the line at 3.37 Å to the line at 3.42 Å is not more than 1.0.

In some cases broadening of lines at d-spacings of 10.3
In some cases broadening of lines at d-spacings of 10.3 ±0.20 Å, 3.86 ±0.08 Å and 3.37 ±0.06 Å may mean that a peak regions. In such instances, the strongest line in the 10.3, 3.86 and 3.37 Angstrom regions should be compared with the strongest line in the 11.15, 3.71 and 3.42 Angstrom regions respectively.

Impurities found in samples of zeolite NU-85 include alpha-quartz and analcime which have XRD lines which coincide with the lines given in Table 1 above. For example, alpha-quartz has its strongest XRD line at 3.34 Å. If present as an impurity in a sample of zeolite NU-85, it will enhance the XRD line at 3.37 Å and therefore, the XRD pattern of the sample will be more akin to that expected for zeolite EU-1. By contrast analcime, found as an impurity in many samples of zeolite NU-85, has a strong line at 3.43 Å in its XRD pattern. If present in a sample of zeolite EU-1, analcime will enhance the XRD line at 3.42 Å with the result that its XRD pattern will resemble the XRD pattern for zeolite NU-85. In view of this it will be readily appreciated by those skilled in the art that care must be exercised in deciding whether a particular sample is zeolite NU-85 based on XRD data alone.

The X-ray powder diffraction data provided herein were obtained with a Philips APD 1700 automated X-ray diffraction system using Cu K-alpha radiation from a long fine focus X-ray tube operating at 40 KV and 50 mA. The radiation was monochromatised by a curved graphite crystal adjacent to the detector. An automatic theta-compensating divergence slit was used with a 0.1 mm receiving slit. Step scanned data were collected between 1 and 60 degrees two-theta. The collected data was analysed in a DEC (Digital Equipment Corporation) Micro PDP −11/73 computer with Philips PW 1867/87 version 3.0 software. The X-ray computer intensities given herein are based on peak height.

The XRD pattern for zeolite NU-85 is similar to that found for zeolite EU-1, except that the former contains certain characteristic lines which have a lower intensity compared to those found for samples of EU-1 prepared according to EP-B-42 226. The three principal lines which fall into this category are those at d-spacings of 10.3 ±0.20; 3.86 ±0.08 and 3.37 ±0.06 Angstroms. Furthermore, the lines at about 10.3 and 3.86 Angstroms are selectively broadened and are shifted to higher d-spacings compared to the corresponding lines in the XRD for EU-1.

The XRD pattern for zeolite NU-85 differs from that found for samples of zeolite NU-87, prepared according to EP-A-377291 in that it does not contain, amongst others, lines at d-spacings of 12.52 ±0.15 and 8.31 ±0.15 Angstroms, which lines are characteristic of zeolite NU-87.

The lattice image data (and electron diffraction data) provided herein were obtained using either a Philips EM400T Transmission Electron Microscope (TEM) operating at 120 KeV or a Philips CM30ST (TEM) operating at 300 KeV. The former has a "point resolution" of 3.7 Å and the latter 2.0 Å. Both instruments were operated using standard conditions appropriate to lattice imaging or to selected area (>0.3 micron diameter) electron diffraction. Electron dose was controlled to minimise beam damage to the zeolite crystals under observation. Damage is not responsible for the structures reported here. The necessary steps were taken to calibrate magnification and camera length (for diffraction) and to employ reproducible microscope conditions. Samples were supported on a holey carbon film and lattice images were recorded from crystals suspended over holes to avoid a confusing background from the support. Lattice images are to be preferred to electron diffraction patterns as a method of determining the structure of NU-85 because this gives direct visual evidence for intergrowths of EU-1 and NU-87; ie there is a 1:1 correspondence between the structure of a crystallite and its lattice image (properly recorded). Lattice images were recorded in a general [uvo] direction relative to the EU-1 unit cell (described in Zeolites, 1988, vol 8, page 74, N. A. Briscoe et al). Bands of EU-1 and NU-87 are imaged without overlap in these directions since the intergrowth plane (001) (in EU-1) is then parallel to the electron beam.

It will be understood by those skilled in the art that it will be necessary to examine a sufficient number of crystals by lattice imaging to ensure that the results obtained are representative of the whole sample. This will be particularly important where a sample is believed to contain a significant amount of either or both of the two parent zeolites, EU-1 and NU-87 together with the intergrowth, or for NU-85 materials which are close to the end-member materials, such as those containing large amounts eg 95% by volume, of EU-1 and small amounts eg 5% by volume of NU-87 in the intergrowth.

The invention is illustrated by FIG. 1 which is a micrograph showing crystals of zeolite NU-85 prepared according to Example 9 hereinafter described. This figure shows a crystal which shows discreet bands of fringes with spacings of 20.2 ± 0.2 and 12.5 ±0.2 Angstroms parallel to one another. In this crystal there are three bands of zeolite NU-87, denoted a, separated by two bands of zeolite EU-1, denoted b. In crystallites showing intergrowth in this sample the proportion of NU-87 (by volume) has been estimated to be about 50%. Only those crystals containing both 20.2 ±0.2 and 12.5 ±0.2 Angstrom fringes were included in this estimate. Some small amount of pure NU-87 does exist in the sample, but the proportion of this has not been estimated.

Figure 2:
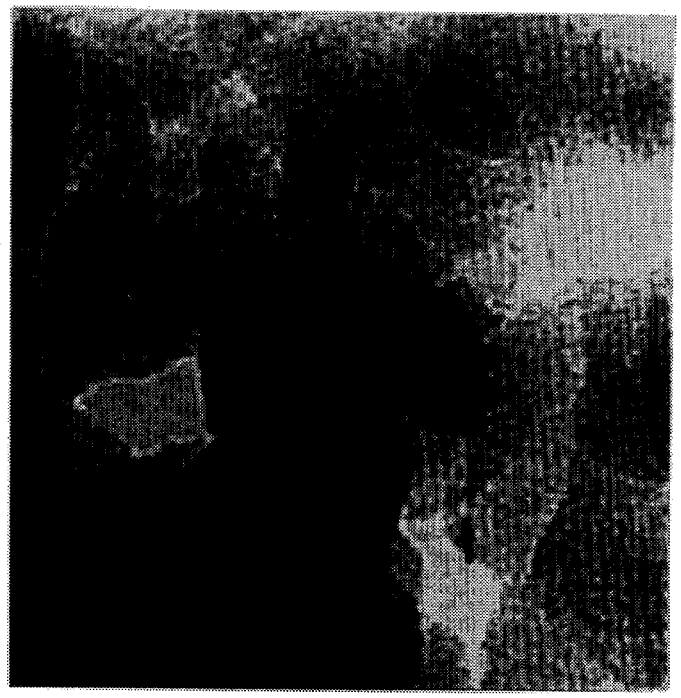
FIG. 2 is a micrograph showing crystals of the zeolite NU-85 prepared according to Example 4.

The invention is also illustrated by FIG. 2 which is a micrograph showing crystals of zeolite NU-85 prepared according to Example 4 hereinafter described. In crystallites showing intergrowth in this sample the proportion of NU-87 (by volume) has been estimated at 30%. As before, only those crystals containing both 20.2 ±0.2 and 12.5 ±0.2 Angstrom fringes were included in this estimate. The reduction in intensity of the characteristic lines in the XRD patterns for these two examples (Nos 9 and 4) are such that the reduction for the material of Example 9 is about twice that for Example 4, which correlates with the volume fractions of NU-87 in intergrowth crystallites referred to above. As the proportion of intergrowth NU-87 in NU-85 falls there will be an increasing proportion of pure EU-1 crystallites in any sample. This is for two related reasons. Firstly the crystallites are of finite size, typically 200-1000A, which means that most crystallites will contain only a few ten's of 20.2 ±0.2 Å layers of EU-1. Secondly the average band width of NU-87 in intergrown crystals appears to be relatively insensitive to total NU-87 content. Hence a small number of crystallites will contain a significant fraction of intergrown NU-87 in EU-1. The corollary is that a sample that contains 1% by volume NU-87 as an intergrowth in EU-1 may contain only 1 in 20 crystallites in a [uvo] orientation which shows any intergrowth. It would then be necessary to examine more than 100 crystallites in the [uvo] orientation to characterise the sample by lattice imaging.

The definition includes as-prepared NU-85 and also forms of it resulting from dehydration and/or calcination and/or ion exchange. The expression "as-prepared" means the product of synthesis and washing with or without drying or dehydration. In its "as-prepared" form NU-85 may include M, an alkali-metal cation, especially sodium and/or ammonium and, when prepared for example from alkylated nitrogen compounds, may include nitrogen-containing organic cations as described below or degradation products thereof or precursors thereof. Such nitrogen-containing organic cations are hereinafter referred to as Q.

Thus zeolite NU-85, as prepared, has the following molar composition, expressed on an anhydrous basis:
100 $XO_2$: less than or equal to 10 $Y_2O_3$: less than or equal to 10 Q: less than or equal to 10 $M_2O$
where Q is the nitrogen-containing organic cation referred to above and M is the alkali metal and/or ammonium cation.

The composition for NU-85 given above is on an anhydrous basis, although "as-prepared" NU-85 and activated forms of NU-85 resulting from calcination and/or ion exchange may contain water. The molar $H_2O$ content of such forms, including as-prepared NU-85, depends on the conditions under which it has been dried and stored after synthesis or activation. The range of molar quantities of contained water is typically between 0 and 100 $XO_2$.

Calcined forms of zeolite NU-85 include no nitrogen-containing organic compound or less than the "as-prepared" form, since the organic material is burned out in the presence of air, leaving hydrogen ion as the other cation.

Among the ion-exchanged forms of zeolite NU-85 the ammonium ($NH_4^+$) form is of importance since it can be readily converted to the hydrogen form by calcination. The hydrogen form and forms containing metals introduced by ion exchange are described below. Under some circumstances exposure of the zeolite of the invention to acid can result in partial or complete removal of a framework element such as aluminium as well as the generation of the hydrogen form. This can provide a means of altering the composition of the zeolite material after it has been synthesised.

The invention also provides a method for the preparation of zeolite NU-85 which comprises reacting an aqueous mixture comprising a source of at least one oxide $XO_2$, a source of at least one oxide $Y_2O_3$, a source of at least one oxide $M_2O$ and at least one nitrogen-containing organic cation Q, or precursors thereof, the mixture preferably having the molar composition:

$XO_2/Y_2O_3$ is within the range 20 to 40, more preferably 25 to 40, most preferably 25 to 35

$(R_1/n)OH/XO_2$ is 0.01 to 2, more preferably 0.05 to 1, most preferably 0.1 to 0.5

$H_2O/XO_2$ is 1 to 500, more preferably 5 to 250, most preferably 25 to 75

$Q/XO_2$ is 0.005 to 1, more preferably 0.02 to 1, most preferably 0.05 to 0.5

$L_pZ/XO_2$ is 0 to 5, more preferably 0 to 1, most preferably 0.05 to 0.5 where X is silicon and/or germanium, Y is one or more of aluminium, iron, boron, titanium, vanadium, zirconium, molybdenum, arsenic, antimony, gallium, chromium, manganese, R is a cation of valency n which can include M, (an alkali metal cation and/or ammonium), and/or Q, (a nitrogen-containing organic cation, or a precursor thereof). In some circumstances it may be an advantage to add a salt $L_pZ$, where Z is an anion of valency p and L is an alkali metal or ammonium ion, which may be the same as M or a mixture of M and another alkali metal or an ammonium ion necessary to balance the anion Z. Z may comprise an acid radical added, for example, as a salt of L or as a salt of aluminium. Examples of Z may include strong acid radicals such as bromide, chloride, iodide, sulphate, phosphate or nitrate or weak acid radicals such as organic acid radicals, for example citrate or acetate. While $L_pZ$ is not essential, it may accelerate the crystalligation of zeolite NU-85 from the reaction mixture and may also affect the crystal size and shape of NU-85. The reaction is continued until crystalligation has occurred.

The preparation is dependent on the temperature at which the reaction is carried out and on the silica to alumina ratio of the reactants in the reaction mixture. Such is the sensitivity to the ratio of $SiO_2/Al_2O_3$ that the source of both the silica and alumina used in the reaction can be an important factor.

Many zeolites have been prepared using nitrogen-containing organic cations or degradation products thereof or precursors thereof and, in particular, polymethylene alpha omega-diammonium cations having the formula:

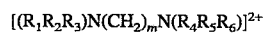

where $R_1$ to $R_6$, which my be the same or different, can be hydrogen, alkyl or hydroxyalkyl groups containing from 1 to 8 carbon atoms, and up to five of the groups can be hydrogen, and m is in the range 3 to 14. For example zeolite EU-1 (EP 42226), zeolite EU-2 (GB 2 077 709) and zeolite ZSM-23 (EP 125 078, GB 2 202 838) have been prepared using such templates.

In the method according to the present invention Q is preferably such a polymethylene alpha, omega-diammonium cation in which m is 6 or 7. M and/or Q can be added as hydroxides or salts of inorganic acids provided the $(R_{1/n})OH/XO_2$ ratio is fulfilled.

Suitable precursors of the nitrogen-containing organic cation Q include the parent diamine with a suitable alkyl halide or the parent dihaloalkane with a suitable trialkylamine. Such materials can be used as simple mixtures or they can be pre-heated together in the reaction vessel, preferably in solution, prior to the addition of the other reactants required for the synthesis of zeolite NU-85.

The preferred cation M is an alkali metal especially sodium, the preferred $XO_2$ is silica ($SiO_2$) and the preferred oxide $Y_2O_3$ is alumina ($Al_2O_3$).

The silica source can be any of those commonly considered for use in synthesising zeolites, for example powdered solid silica, silicic acid, colloidal silica or dissolved silica. Among the powdered silicas usable are precipitated silicas, especially those made by precipitation from an alkali metal silicate solution, such as the type known as "KS 300" made by AKZO, and similar products, aerosil silicas, fumed silicas "CAB-O-SIL" and silica Eels suitably in grades for use in reinforcing pigments for rubber and silicone rubber. Colloidal silicas of various particle sizes may be used, for example 10–15 or 40–50 microns, as sold under the Registered Trade Marks "LUDOX", "NALCOAG" and "SYTON". The usable dissolved silicas include commercially available waterglass silicates containing 0.5 to 6.0, especially 2.0 to 4.0 mols of $SiO_2$ per mol of alkali metal oxide, "active" alkali metal silicates as defined in British Patent 1193254, and silicates made by dissolving silica in alkali metal hydroxide or quaternary ammonium hydroxide or a mixture thereof.

The optional alumina source is most conveniently sodium aluminate, or aluminium, an aluminium salt, for example the chloride, nitrate or sulphate, an aluminium alkoxide or alumina itself, which should preferably be in a hydrated or hydratable form such as colloidal alumina, pseudoboehmite, boehmite, gamma alumina or the alpha or beta trihydrate. Mixtures of the above can be used.

Optionally all or some of the alumina and silica source may be added in the form of an aluminosilicate.

The reaction mixture is usually reacted under autogenous pressure, optionally with added gas, e.g. nitrogen, at a temperature of less than 190° C. and more than 85° C., preferably not more than 180° C. and not less than 120° C. and most preferably not more than 160° C., until crystals of zeolite NU-85 form, which can be from 1 hour to many months depending on the reactant composition and the operating temperature. Agitation is optional, but is preferable since it reduces the reaction time and can improve product purity.

The use of seed material can be advantageous in decreasing the time to nucleation and/or overall crystallisation time. It may also be an advantage in encouraging the formation of NU-85 at the expense of an impurity phase. Such seed materials include zeolites, especially crystals of zeolite NU-85, zeolite NU-87, zeolite EU-1 or mixtures thereof. The seed crystals are usually added in an amount of between 0.01 and of the weight of silica used in the reaction mixture.

At the end of the reaction, the solid phase is collected in a filter and washed, and is then ready for further steps such as drying, dehydration and ion exchange.

If the product of the reaction contains alkali metal ions, these have to be at least partly removed in order to prepare the hydrogen form of NU-85 and this can be done by ion-exchange with an acid, especially a mineral acid such as hydrochloric acid, or by way of the ammonium compound, made by ion exchange with a solution of an ammonium salt such as ammonium chloride. Ion exchange may be carried out by slurrying once or several times with the ion exchange solution. The zeolite is usually calcined before ion exchange to remove any occluded organic matter since this usually facilitates ion exchange.

In general, the cation(s) of zeolite NU-85 can be replaced by any cation(s) of metals, and particularly those in groups 1A, 1B, IIA, IIB, IIIA, IIIB (including rare earths) and VIII (including noble metals) of the Periodic Table, other transition metals and by tin, lead and bismuth. (The Periodic Table is as in "Abridgements of Specifications" published by the UK Patent Office). Exchange is normally carried out using a solution containing a salt of the appropriate cation.

When compared to the parent zeolites, EU-1 and NU-87, zeolite NU-85 is cheaper to produce than zeolite NU-87, owing to the relative costs of the respective preferred templates (m=6 as compared to m=10) and increased reaction rates, and it exhibits greater catalytic activity than EU-1. The enhanced catalytic activity at relatively low costs makes NU-85 an attractive commercial catalyst for many applications for which NU-87, because of its higher cost, would not be considered. The molecular sieving effect of zeolite NU-85 is also different from that for zeolite NU-87.

The invention is further illustrated by the following examples.

EXAMPLE 1 (Comparative)

Preparation of EU-1

A reaction mixture of molar composition:

$60SiO_2$—$0.77Al_2O_3$—$10Na_2O$—$10\ HexBr_2$—$3000\ H_2O$ was prepared from:

51.5 g "CAB-O-SIL" (BDH Ltd)

3.322 g Sodium Aluminate (BDH Ltd: molar composition $1.37Na_2O$—$Al_2O_3$—$6.37H_2O$)

10.22 g Sodium Hydroxide 51.7 g $HexBr_2$ 767.6 g Water where $HexBr_2$ is Hexamethonium Bromide:

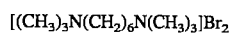

$[(CH_3)_3N(CH_2)_6N(CH_3)_3]Br_2$

The mixture was prepared as follows:
A—solution containing the sodium hydroxide and sodium aluminate in about one third of the total water
B—solution containing $HexBr_2$ in about one third of the water
C—dispersion of "CAB-O-SIL" in the remaining water.

Solutions A and B were added, with stirring, to dispersion C. Stirring was continued until a smooth gel was obtained. The resulting mixture was transferred to a 1 litre stainless steel autoclave and reacted at 210° C., with stirring at 300 rpm using a pitched-paddle type impeller.

After 25 hours at reaction temperature the preparation was crash cooled to ambient temperature and the product discharged. The product was filtered, washed with demineralised water and then dried at 110° C.

Analysis for Al, Na and Si revealed the following molar composition:

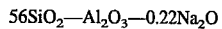

$56SiO_2$—$Al_2O_3$—$0.22Na_2O$

The product was analysed by X-ray powder diffraction and identified as zeolite EU-1. The interplanar spacings and intensities are give in Table 2.

Scanning electron microscopy showed ellipsoidal particles, most of which were 1–10 microns in length. The particles did not appear to be single crystals but looked to be composed of aligned plate or lath-like crystals.

EXAMPLE 2 (Comparative)

Preparation of EU-1

A reaction mixture of molar composition:

$60SiO_2$—$1.5Al_2O_3$—$10Na_2O$—$10HexBr_2$—$3000H_2O$
was prepared from:

171.7 g "SYTON X30" (Monsanto: a colloidal silica solution containing 30% silica)

6.172 g Sodium Aluminate (BDH Ltd: molar composition $1.37Na_2O$—$Al_2O_3$—$5.61H_2O$)

9.08 g Sodium Hydroxide 134.0 g $HexBr_2$ solution (containing 38.6 %w/w $HexBr_2$ in water)

565.4 g Water

The molar composition given does not include sodium present in the "SYTON X30"

The mixture was prepared as follows:

A—solution containing the sodium hydroxide and sodium aluminate in 250 g of water B—solution containing $HexBr_2$ in 150 g of water C—dispersion of "SYTON X30" in the remaining water.

Solution A was added to solution B and the resulting solution added, with stirring, to dispersion C. Stirring was continued until a smooth gel was obtained. The resulting mixture was transferred to a 1 litre stainless steel autoclave and reacted at 160° C., with stirring at 300 rpm using a pitched-paddle type impeller.

After 10 days at reaction temperature the preparation was crash cooled to ambient temperature and the product discharged. The product was filtered off, washed with demineralised water and then dried at 110° C.

The product was analysed by X-ray powder diffraction and identified as zeolite EU-1. The diffraction pattern is given in FIG. 3 and the interplanar spacings and intensities are given in Table 3.

EXAMPLE 3

A reaction mixture of molar composition:

$60SiO_2$—$1.714Al_2O_3$—$10Na_2O$—$10HexBr_2$—$3000H_2O$
was prepared from:

51.5 g "CAB-O-SIL" (BDH Ltd)

6,800 g Sodium Aluminate (BDH Ltd: molar composition $1.31Na_2O$—$Al_2O_3$—$5.25H_2O$)

8.86 g Sodium Hydroxide 134.0 g $HexBr_2$ solution (containing 38.6 % w/w $HexBr_2$ in water)

684.2 g Water

The mixture was prepared as follows:

A—solution containing the sodium hydroxide and sodium aluminate in 250g of water B—solution containing $HexBr_2$ in 170 g of water C—dispersion of "CAB-O-SIL" in the remaining water.

Solutions A and B were mixed together and then added, with stirring, to dispersion C. Stirring was continued until a smooth gel was obtained. The resulting mixture was transferred to a 1 litre stainless steel autoclave and reacted at 160° C., with stirring at 300 rpm using a pitched-paddle type impeller.

The preparation was sampled daily. After 261 hours at reaction temperature the preparation was crash cooled to ambient temperature and the product discharged. The product was filtered, washed with demineralised water and then dried at 110° C.

Analysis for Al, Na and Si revealed the following molar composition:

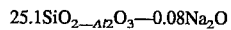
$25.1SiO_2$—$Al_2O_3$—$0.08Na_2O$

The product was analysed X-ray powder diffraction and identified as zeolite NU-85. The diffraction pattern is given in FIG. 4 and the interplanar spacings and intensities in Table 4.

Figure 3:
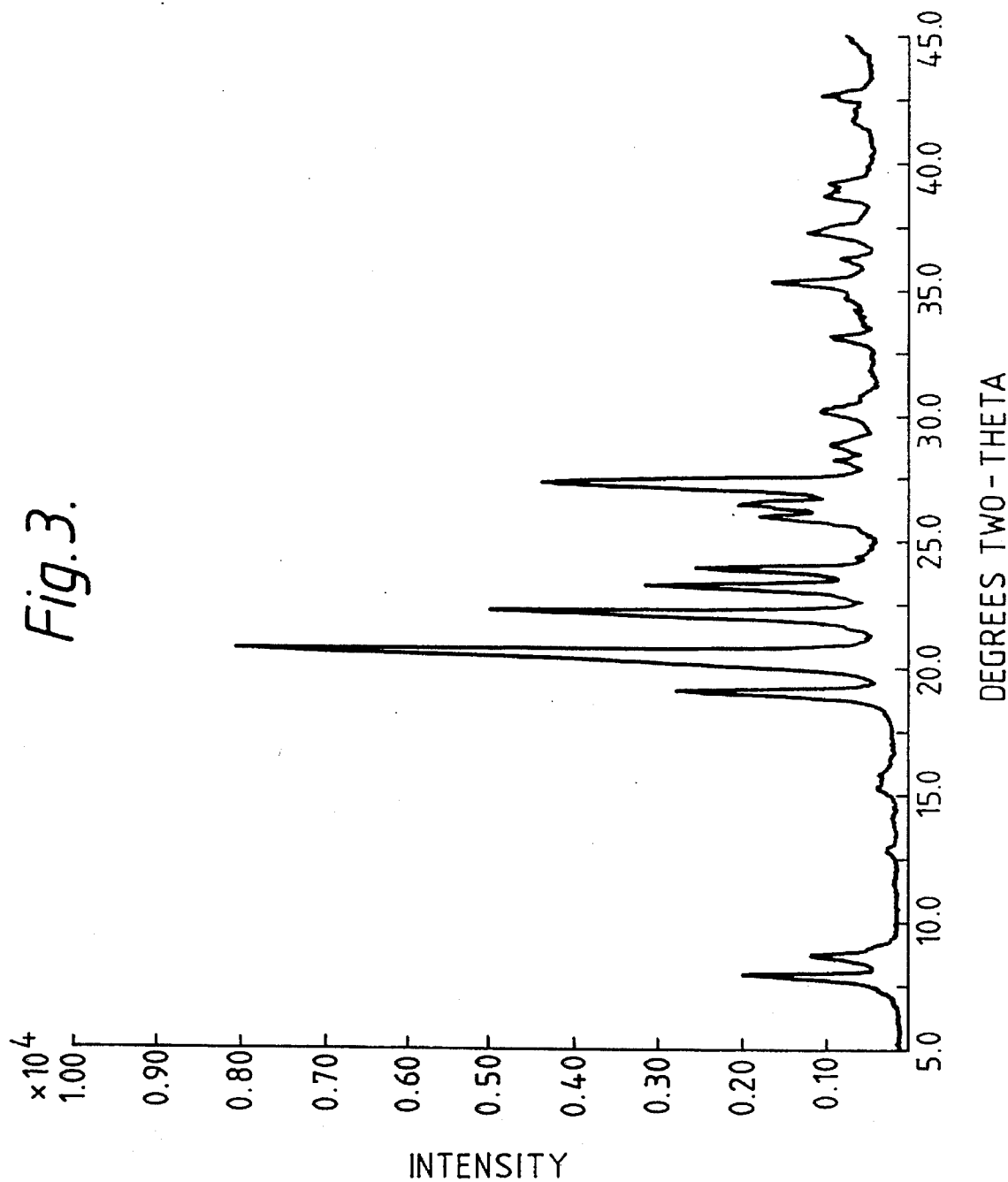
FIG. 3 illustrates the X-ray powder diffraction pattern for zeolite EU-1 identified in comparative Example 2.
Figure 4:
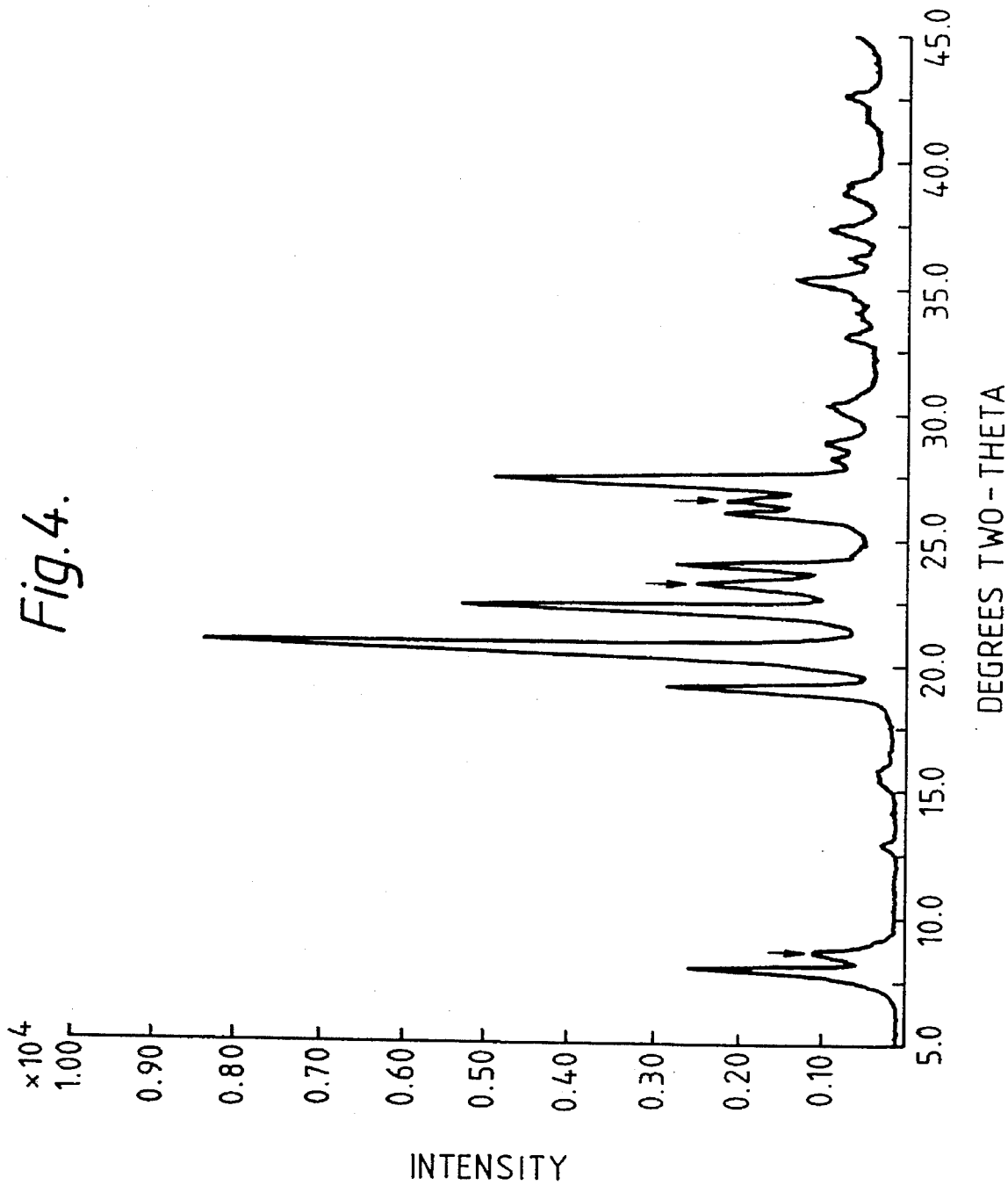
FIG. 4 shows the X-ray powder diffraction pattern of NU-85 in Example 3.

Examination of FIG. 4 and Table 4 and comparison with FIG. 3 and Tables 2 and 3 indicates some differences in the marked regions. Most significant is the reduction in intensity of the line at about 23 degrees two-theta (d-spacing of about 3.85 Å).

The reduction in intensity is most noticeable for this line because the shape of the pattern in the 20.5 to 25 degrees two-theta region (d-spacing of 4.33 to 3.56 Å) is altered, with the successive step-wise decrease in intensity for the three lines at the low-angle side of the 20.5 degrees two-theta line (d-spacing of 4.33 Å), being changed to a pattern in which the 23 degrees two-theta line (d-spacing of 3.85 A) has an intensity lower than that of the 24 degrees two-theta line (d-spacing of 3.7 Å).

Additionally, the intensity of the line at about 8.6 degrees two-theta (d-spacing of 10.24 Å) is reduced to less than half the intensity of the line at about 8 degree two-theta (d-spacing of 11.15 Å). Furthermore, the intensity of the line at about 26.5 degrees two-theta (d-spacing of 3.37 Å) is reduced to a value less than the intensity of the line at 26 degrees two-theta (d-spacing of 3.43 Å).

Example 3 illustrates that zeolite NU-85 can be prepared from reagents which give zeolite EU-1 provided the correct combination of aluminium content and reaction temperature is employed.

The following examples illustrate the effect of crystallisation temperature on the formation of zeolite NU-85.

EXAMPLE 4

A reaction mixture of molar composition:

$60SiO_2$—$1.714Al_2O_3$—$10Na_2O$—$10HexBr_2$—$3000H_2O$ was prepared from:

801 g "CAB-O-SIL" (BDH Ltd)

114.8 g Sodium Aluminate (BDH Ltd: molar composition $1.37Na_2O$—$Al_2O_3$—$6.37H_2O$)

136 g Sodium Hydroxide 805 g $HexBr_2$ 11.925 kg Water

The mixture was prepared as follows:

A—solution containing the sodium hydroxide and sodium aluminate in 2 kg of water B—solution containing $HexBr_2$ in 1.925 kg of water C—dispersion of "CAB-O-SIL" in the remaining water.

Dispersion C was charged to a 19 litre autoclave followed by solution B. Finally solution A was charged to the autoclave. The mixture was reacted at 160° C. with stirring at 300 rpm using a flat paddle stirrer.

The preparation was sampled daily. After 11 days at reaction temperature the preparation was crash cooled to ambient temperature and the product discharged. The product was filtered, washed with demineralised water and then dried at 110° C.

The product was analysed by X-ray powder diffraction and identified as zeolite NU-85. The diffraction pattern is given in FIG. 5 and the interplanar spacings and intensities in Table 5.

A micrograph showing crystals of this example is given in FIG. 2.

EXAMPLE 5

Example 4 was repeated except that the reaction was carried out at 180° C. for 69 hours. The product was analysed by X-ray powder diffraction and identified as zeolite NU-85. The diffraction pattern is given in FIG. 6 and the interplanar spacings and intensities in Table 6.

EXAMPLE 6 (Comparative)

Preparation of zeolite EU-1

Example 4 was repeated except that the reaction was carried out at 200° C. for 20 hours.

Figure 7:
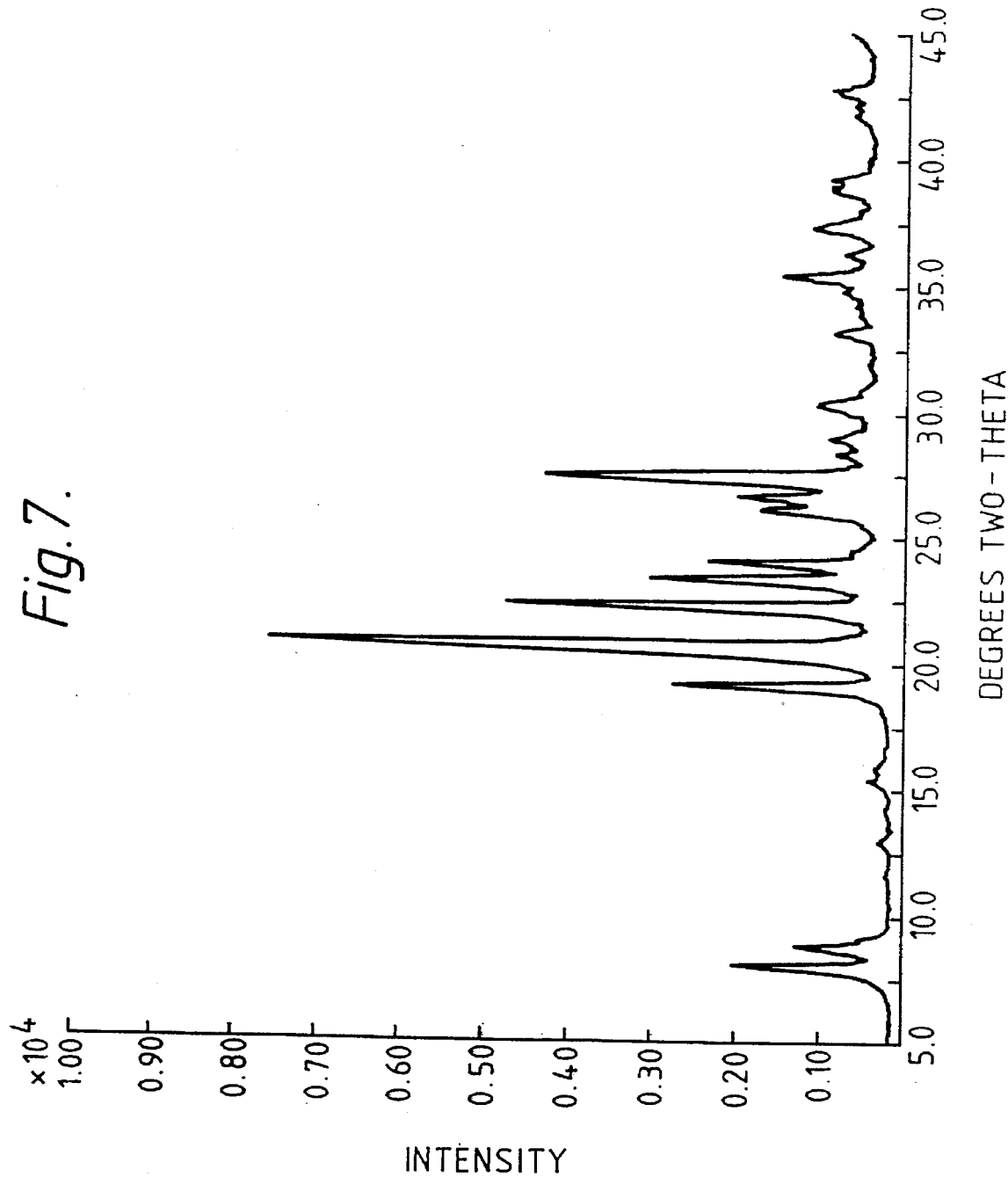
FIG. 7 shows the X-ray powder diffraction pattern of "as-prepared" EU-1.

The product was analysed by X-ray powder diffraction and identified as zeolite EU-1. The diffraction pattern is given in FIG. 7 and the interplanar spacings and intensities in Table 7.

An examination and comparison of Examples 4 to 6 shows the importance of the crystallisation temperature in the preparation of zeolite NU-85. For the particular reaction conditions employed, a crystallisation temperature of 200° C. resulted in the production of zeolite EU-1 whereas, when the temperature was reduced to 160° C. zeolite NU-85 was produced. Thus, as the temperature was reduced the product changed from pure EU-1 to an intergrowth of the zeolites EU-1 and NU-87.

Example 5 demonstrates that the transition temperature, that is the temperature at which the intergrowth forms in preference to pure EU-1, is close to 180° C. since the XRD of the product from this example (FIG. 6 and Table 6) shows some of the features which are characteristic of zeolite NU-85. In particular, the ratio of the intensity of the line at 10.16 Å (8.5 degrees two-theta) to the line at 11.09 Å (8 degrees two-theta) is 0.5, rounded to one decimal place. Furthermore, the ratio of the intensity of the line at 3.84 Å (23 degrees two-theta) to the intensity of the line at 3.71 Å (24 degrees two-theta) is 1.05, ie 1.1 rounded to one decimal place.

EXAMPLE 7

It is well known that the thermal history of a particular zeolite can alter the relative intensities observed in its X-ray powder diffraction pattern. This has been observed for many zeolites including ZSM-5 (E. L. Wu, S. L. Lawton, D. H. Olson, A. C. Rohrman, Jr and G. T. Kokotailo, J Phys Chem, 1979, 83, 2777) and Nu-3 (G. D. Short and T. V. Whittam, European Patent 40 016). Indeed, some minor changes have been reported for EU-1 itself (J. L. Casci, T. V. Whittam and B. M. Lowe, "Proc VI Zeolite Conf", Butterworths, 1984, 894).

In order to show that the features in the X-ray powder diffraction pattern found for samples of zeolite NU-85 was not due to the thermal history or associated with the occluded template, a portion of the product from both Examples 4 and 6 was calcined in air at 450° C. for 24 hours followed by 24 hours at 550° C. The X-ray powder diffraction patterns of the calcined material from Examples 4 and 6 can be seen in FIGS. 8 and 9 respectively.

A comparison of the X-ray powder diffraction pattern for the calcined sample of EU-1 (FIG. 9) with that for the "as prepared" material (FIG. 7) shows some differences. In particular, in FIG. 9 (calcined EU-1) there is an increase in the relative intensity of the low angle lines compared to those in the mid angle region. However, the general pattern of the lines remains the same as does the order of the intensities of the cluster of peaks in the region 20 to 25 degrees two theta.

A comparison of the X-ray powder diffraction pattern for the calcined sample of zeolite NU-85 (FIG. 8) with that for the "as prepared" material (FIG. 5) also shows an overall increase in intensity of the low angle lines relative to those in the mid-angle region.

Figure 8:
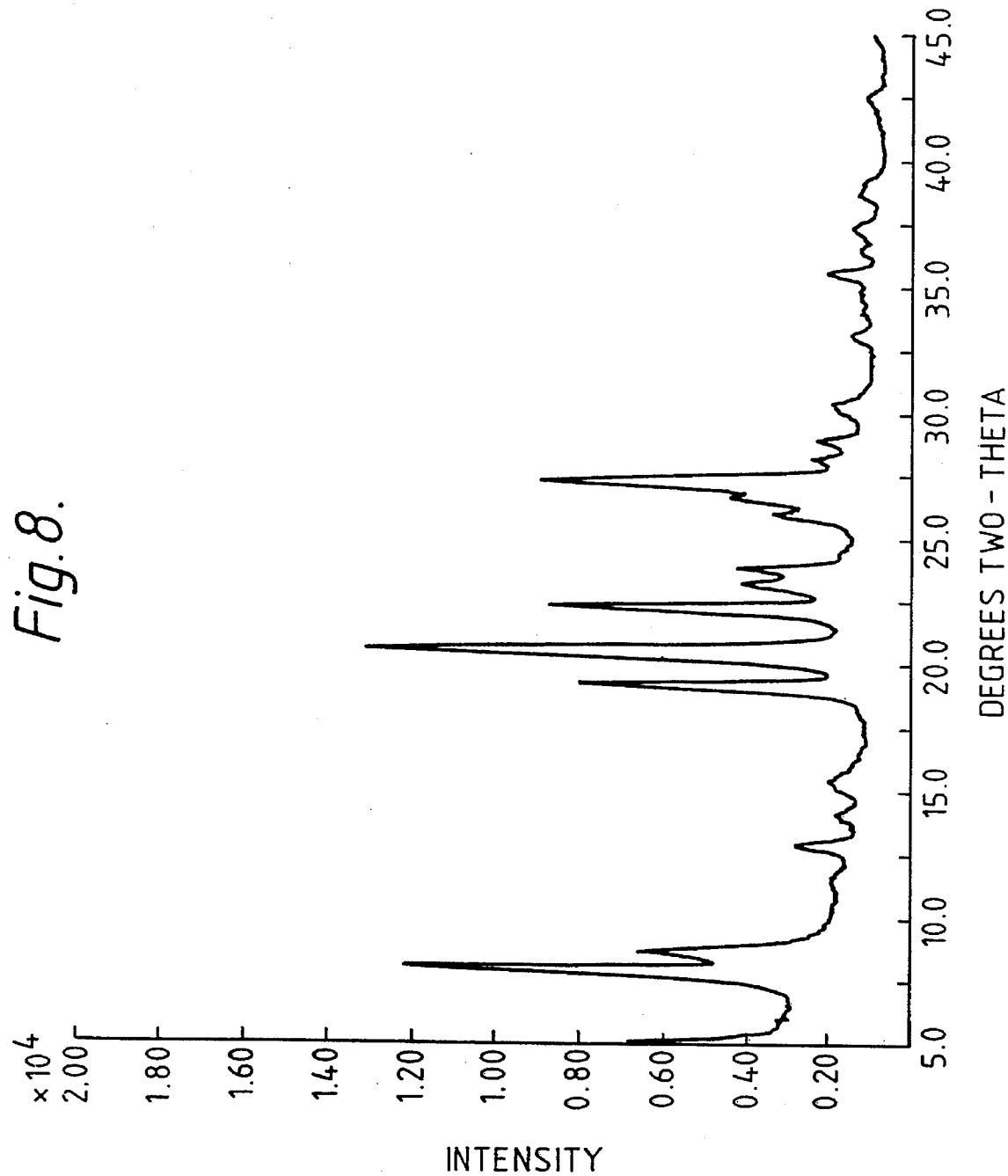
FIG. 8 shows the X-ray powder diffraction pattern of the calcined zeolite NU-85 from Example 4.
Figure 9:
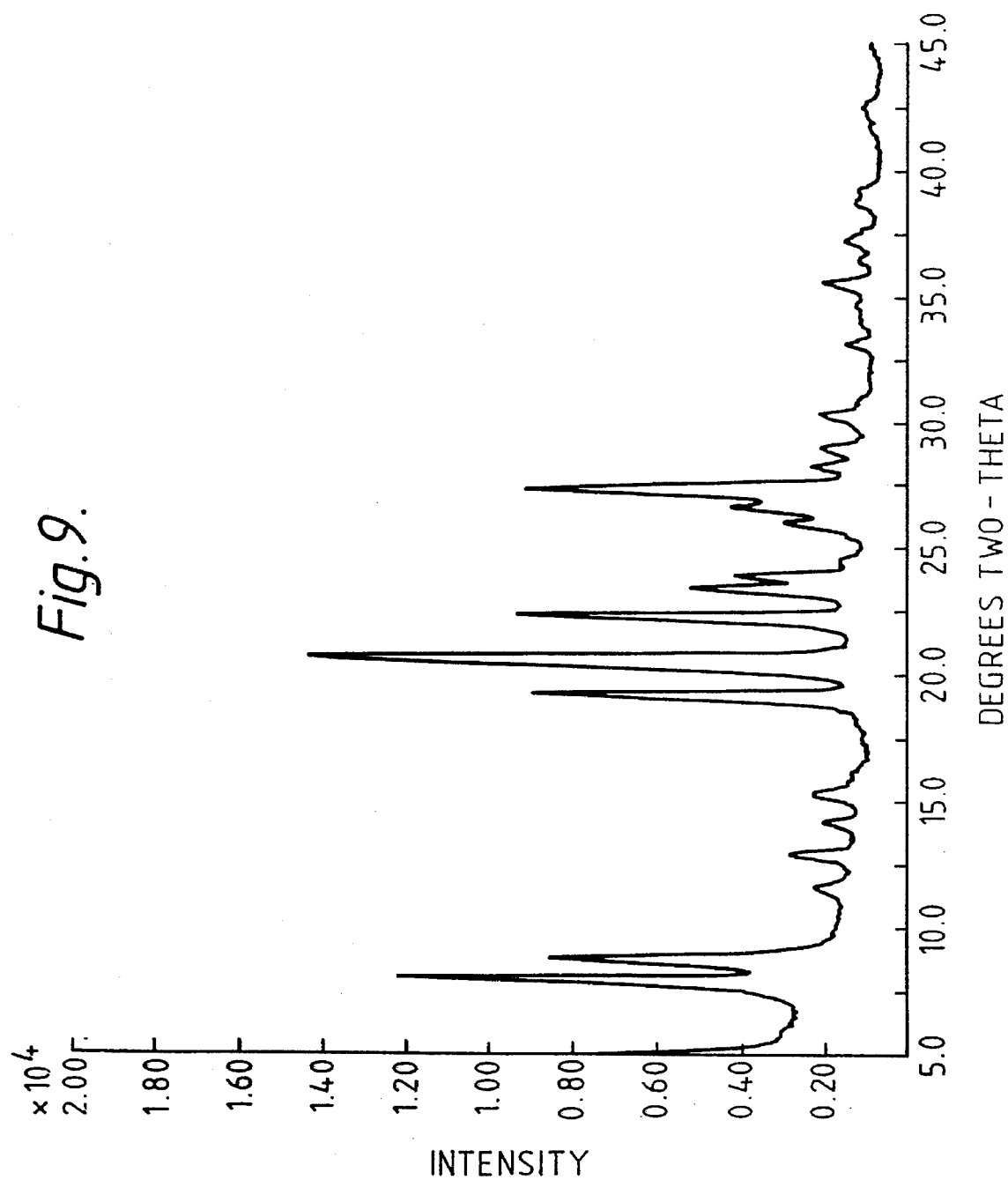
FIG. 9 shows the X-ray powder diffraction pattern of the calcined EU-1 from Example 6.

A comparison of FIG. 8 (calcined sample of zeolite NU-85) with FIG. 9 (calcined sample of zeolite EU-1) reveals the same difference that was found from a comparison of the X-ray powder diffraction patterns of the "as prepared" materials (FIG. 4, Table 4 with FIG. 3 and Tables 2 and 3). In particular, whereas for zeolite NU-85 the line at 3.8 Å (23.5 degrees two-theta) has a lower intensity than the line at 3.7 Å (24 degrees two-theta), for zeolite EU-1 the reverse is found.

EXAMPLE 8

This example demonstrates that zeolite NU-85 is not solely due to some compositional difference.

Analysis for Al, Na and Si of the sample of zeolite EU-1 prepared in Example 6 revealed the following molar composition:

$$26.5SiO_2 - Al_2O_3 - 0.16Na_2O$$

This can be compared with the molar composition found for zeolite NU-85 prepared according to Example 3 which was:

$$25.1SiO_2 - Al_2O_3 - 0.08Na_2O$$

The similarity between these compositions is such that the differences in X-ray powder diffraction patterns can not be attributed to the these compositional differences.

Since zeolite NU-85 is an intergrowth of two phases it is possible to have a material which comprises a continuum between the pure end-members, zeolite EU-1 and zeolite NU-87, and in which the continuum comprises EU-1 intergrown to different extents with NU-87. Another possible material would include the intergrowth (zeolite NU-85) together with either or both of the parent zeolites as an impurity, that is a physical mixture of zeolites NU-85 with zeolites EU-1 and NU-87.

The following example illustrates the preparation of zeolite NU-85 which contains a higher proportion of NU-87 than the material made according to Example 3. (This is based on the assumption that the ratio of the intensity of the XRD line at 3.8 Å to the intensity of the line at 3.78 is inversely proportional to the amount of zeolite NU-87 present in the intergrowth).

EXAMPLE 9

A reaction mixture of molar composition:

$$60SiO_2 - 2.18Al_2O_3 - 10Na_2O - 10HexBr_2 - 3000H_2O$$
$$60SiO_2 - 2.18Al_2O_3 - 10Na_2O - 10HexBr_2 - 3000H_2O$$

343.3 g "SYTON X30" (Monsanto: a colloidal silica solution containing 30% silica)

17.50 g Sodium Aluminate (BDH Ltd: molar composition 1.23Na$_2$O—Al$_2$O$_3$—5.70H$_2$O)
16.73 g Sodium Hydroxide
268.1 g HexBr$_2$ solution (containing 38.6%w/w HexBr$_2$ in water)
1129.1 g Water The molar composition given does not include sodium present in the "SYTON X30".

The mixture was prepared as follows:
A—solution containing the sodium hydroxide and sodium aluminate in 500 g of water
B—solution containing HexBr$_2$ in 300 g of water
C—dispersion of "SYTON X30" in the remaining water.

Solutions A and B were mixed and added, with stirring, to dispersion C. Stirring was continued until a smooth mixture was obtained. The resulting mixture was transferred to a 2 litre stainless steel autoclave and reacted at 160° C., with stirring at 300 rpm. (Due to fault in the system the heater was switched off for six hours after a reaction time of 74 hours).

After 450 hours at reaction temperature the preparation was crash cooled to ambient temperature and the product discharged. The product was filtered, washed with demineralised water and then dried at 110° C.

Figure 5:
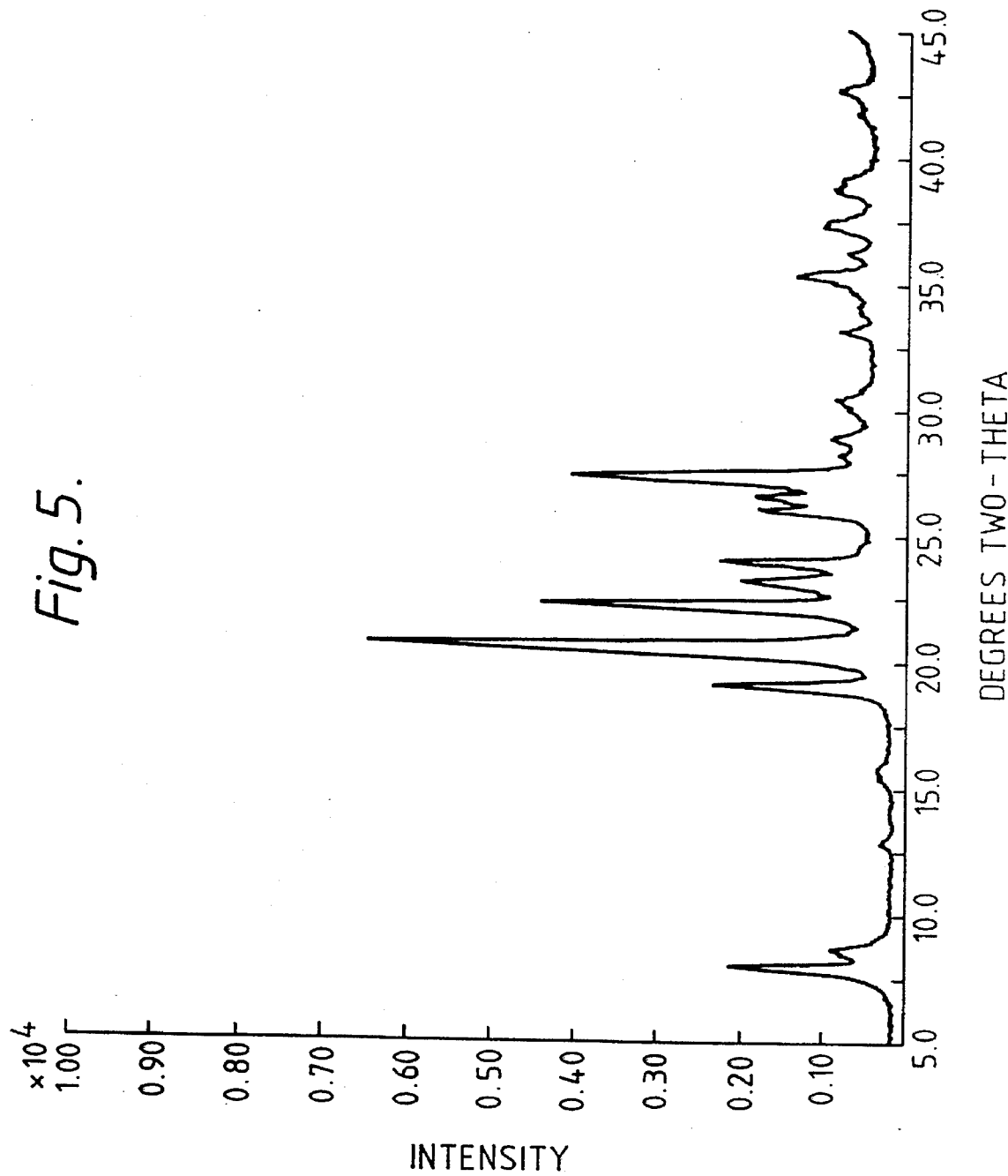
FIG. 5 gives the X-ray powder diffraction pattern for zeolite NU-85 of Example 4.
Figure 6:
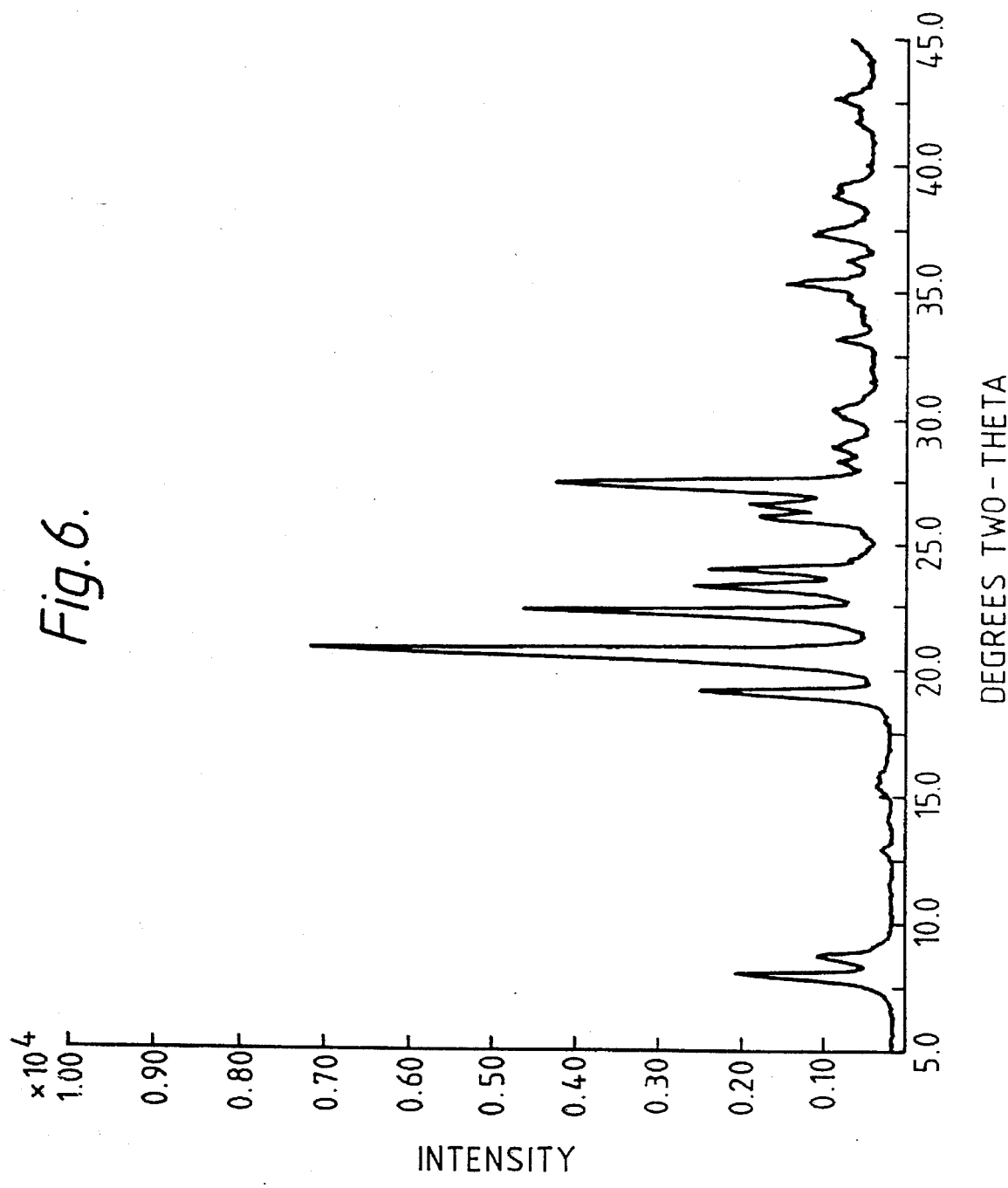
FIG. 6 shows the X-ray diffraction pattern for the product identified as zeolite NU-85 in Example 5.
Figure 10:
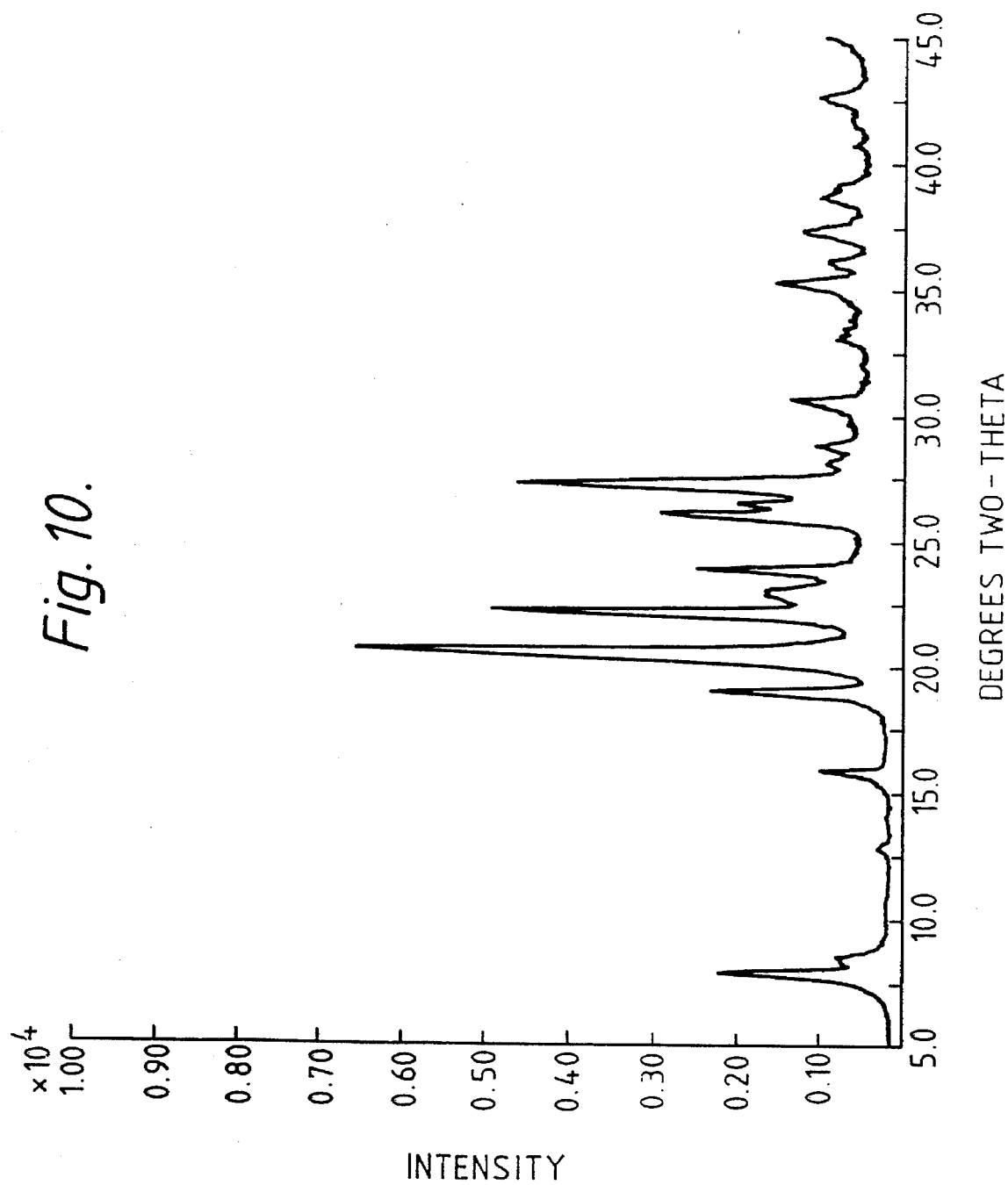
FIG. 10 shows the X-ray powder diffraction pattern for the zeolite NU-85 product of Example 9.

The product was analysed by X-ray powder diffraction. The diffraction pattern is given in FIG. 10 and the interplanar spacings and intensities in Table 8. A comparison of FIG. 10 with FIGS. 4 to 6 shows the product was zeolite NU-85. The sample contained about 5% w/w of an analcime as an impurity. A micrograph showing crystals of this example is given in FIG. 1.

EXAMPLE 10

A reaction mixture of molar composition:
60SiO$_2$—2.18Al$_2$O$_3$—10Na$_2$O—10HexBr$_2$—3000H$_2$O
was prepared from:
"SYTON X30" (Monsanto: a colloidal silica sol containing 30% silica)
Sodium Aluminate (BDH Ltd: 27.5% Na$_2$O, 34.6%Al$_2$O$_3$,
Sodium Aluminate (BDH Ltd: 27.5% Na$_2$O, 34.6%Al$_2$O$_3$,
Sodium Hydroxide (31.1%w/v solution)
HexBr$_2$ solution (containing 38.6%w/w HexBr$_2$ in water)
Water The molar composition given does not include any sodium present in the "SYTON X30".

The mixture was prepared as follows:
A—solution containing the sodium hydroxide and sodium aluminate in water B—solution containing HexBr$_2$ in water C—dispersion of "SYTON X30" in water Dispersion C was charged to the reactor followed by solution B. Finally solution A was charged to the reactor. Water was flushed through the pipes to the reactor in between additions of A, B and C.

The mixture was reacted at 160° C. with stirring at about 140 rpm using a four-blade pitched paddle type impeller.

After 427 hours at reaction temperature the preparation was terminated and crash cooled to ambient temperature. The product was then filtered, washed with condensate and dried.

Figure 11:
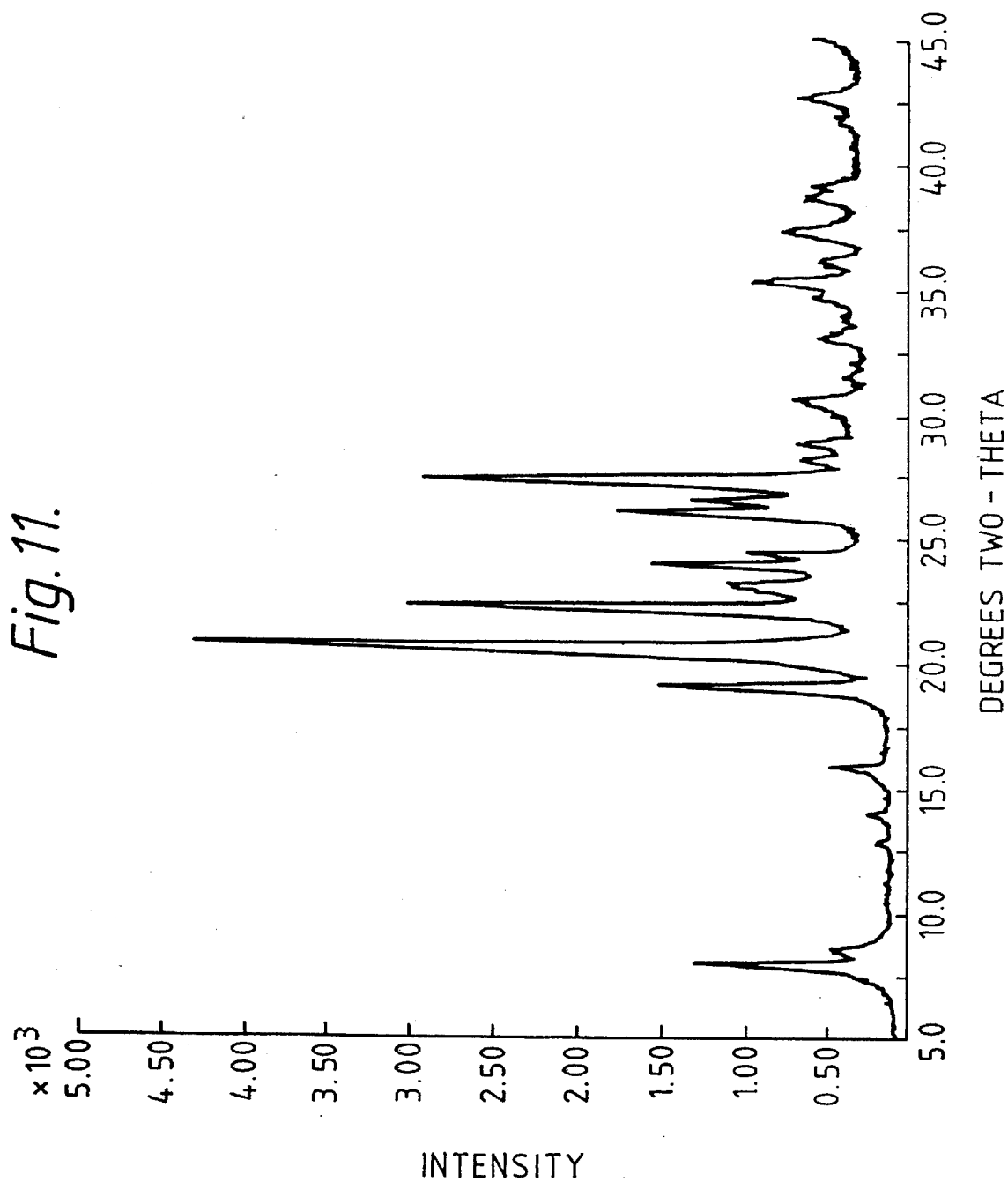
FIG. 11 shows the X-ray powder diffraction pattern for zeolite NU-85 of Example 10.

Analysis for Al, Na, and Si revealed the following molar composition:
20.2SiO$_2$—Al$_2$O$_3$—0.28Na$_2$O The product was analysed by X-ray powder diffraction. The diffraction pattern is given in FIG. 11 and the interplanar spacings and intensities in Table 9. The product was found to be a highly crystalline sample of zeolite NU-85 containing small amounts, less than 5% of each of analcime and sodalite as impurities.

EXAMPLE 11

A reaction mixture of molar composition:
60SiO$_2$—2Al$_2$O$_3$—10Na$_2$O—10HeptaBr$_2$—3000H$_2$O was prepared from:
51.5 g "CAB-O-SIL" (BDH Ltd)
8.229 g Sodium Aluminate (BDH Ltd: 35.4%w/w Al$_2$O$_3$,
8.229 g Sodium Aluminate (BDH Ltd: 35.4%w/w Al$_2$O$_3$, 29.5%w/w Na20, 35.1% w/w H$_2$O)
138.2 g HeptaBr$_2$ solution (containing 38.9% w/w HeptaBr$_2$ in water)
682.8 g Water
where HeptaBr$_2$ is Heptamethonium Bromide

[(CH$_3$)$_3$N(CH$_2$)$_7$N(CH$_3$)$_3$]Br$_2$

The mixture was prepared as follows:
A—solution containing the sodium hydroxide and sodium aluminate in 250 g of water
B—solution containing HeptaBr$_2$ in 170 g of water
C—dispersion of "CAB-O-SIL" in the remaining water.

Solutions A and B were mixed together and then added, with stirring, to dispersion C. Stirring was continued until a smooth gel was obtained. The resulting mixture was transferred to a 1 litre stainless steel autoclave and reacted at 160° C., with stirring at 300 rpm using a pitched-paddle type impeller.

The preparation was sampled periodically. After 432 hours at reaction temperature the reaction was terminated, crash cooled to ambient temperature and the product discharged. The product was filtered, washed with demineralised water and then dried at 110° C.

Analysis for Al, Na and Si revealed the following molar composition:

25.1 SiO$_2$—Al$_2$O$_3$—0.20Na$_2$O

The product was analysed by X-ray powder diffraction and found to be a sample of NU-85 containing approximatley 6%w/w of an Analcime impurity. The computer derived intensities for the lines which are diagnostic of NU-85 were as follows:

|  | Spacing/Å | Intensities | Ratio of intensities (rounded to one decimal place) |
| --- | --- | --- | --- |
| relationship (b) | 3.86 vs 3.71 | 23.8 vs 36.7 | 0.6 |
| relationship (a) | 10.3 vs 11.5 | 9.7 vs 38.7 | 0.3 |
| relationship (c) | 3.37 vs 3.42 | 26.6 vs 45.0 | 0.6 |

The presence of Analcine in the sample means that relationship (c) cannot be used to identify the product.

EXAMPLE 12

A reaction mixture of molar composition:
60SiO$_2$—1.714Al$_2$O$_3$—10Na$_2$O—10HexBr$_2$—3000H$_2$O was prepared from:
801 g "CAB-O-SIL" (BDH Ltd)
105.8 g Sodium Aluminate (BDH Ltd, molar composition 1.31Na$_2$O—Al$_2$O$_3$—5.25H$_2$O)
137.9 g Sodium Hydroxide
805 g HexBr$_2$
11.924 kg Water The mixture was prepared as follows:

A—solution containing the sodium hydroxide and sodium aluminate in 2 kg of water
B—solution containing HexBr$_2$ in 1.924 kg of water
C—dispersion of "CAB-O-SIL" in the remaining water.

Dispersion C was charged to a 19 litre autoclave followed by solution B. Finally solution A was charged to the autoclave. The mixture was reacted at 150° C., with stirring at 300 rpm using a flat paddle stirrer.

The preparation was sampled periodically. After 23 days at reaction temperature the preparation was crash cooled to ambient temperature and the product discharged. The product was filtered, washed with demineralised water and then dried at 110° C.

Analysis for Al, Na and Si revealed the following molar composition:-

$$28.5SiO_2—Al_2O_3—0.05Na_2O$$

Figure 12:
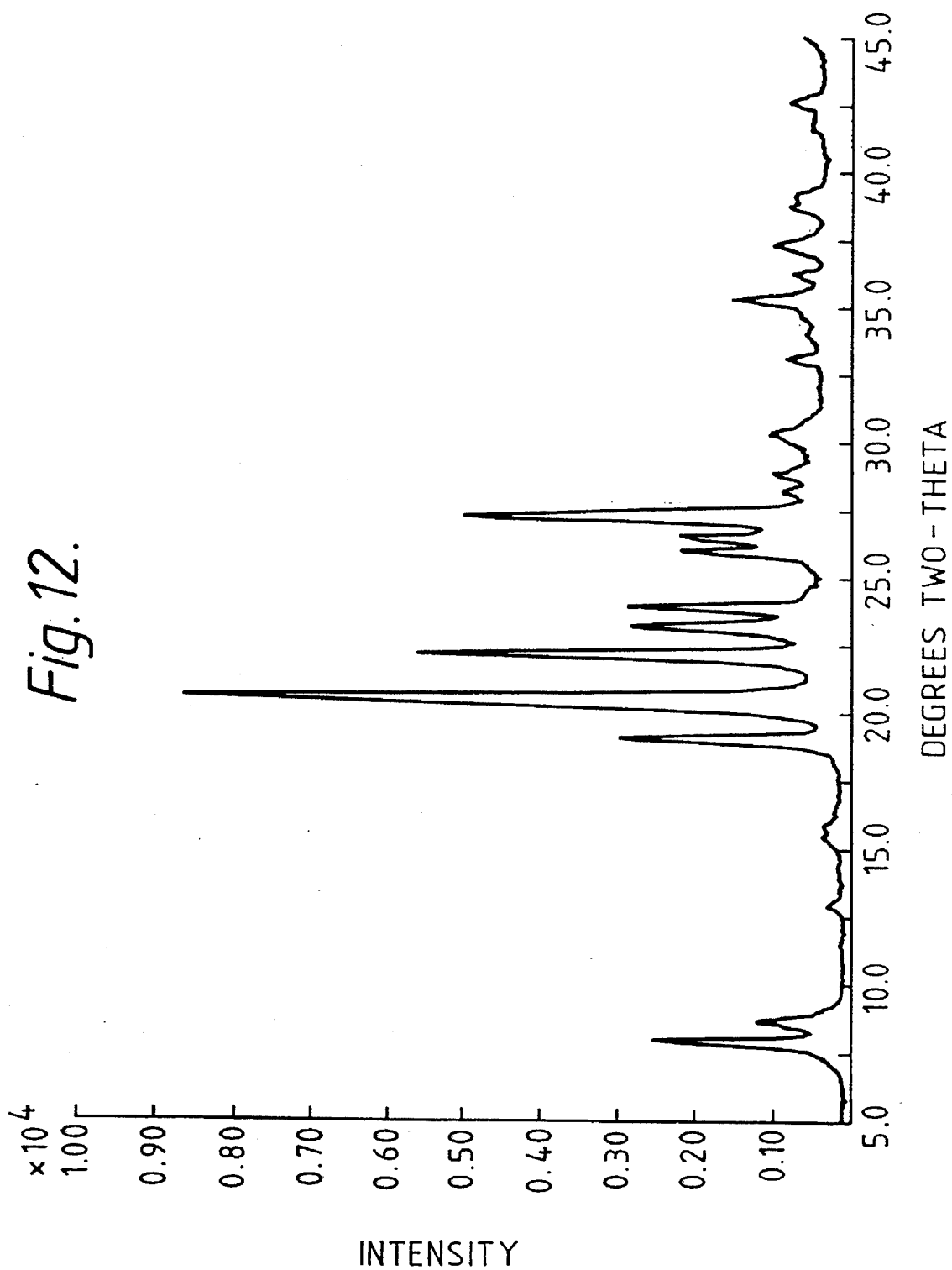
FIG. 12 illustrates the X-ray powder diffraction pattern for zeolite NU-85 in Example 12.

The product was analysed by X-ray powder diffraction and found to be a highly crystalline sample of NU-85 containing no detectable crystalline impurities. The diffraction pattern is given in FIG. 12. The computer derived intensities for the lines which are diagnostic of zeolite NU-85 are as follows:

|  | Spacing/Å | Intensities | Ratio of intensities (rounded to one decimal place) |
|---|---|---|---|
| relationship (b) | 3.8 vs 3.7 | 29.9 vs 29.0 | 1.0 |
| relationship (a) | 10.2 vs 11.2 | 12.5 vs 28.1 | 0.4 |
| relationship (c) | 3.35 vs 3.42 | 21.2 vs 18.9 | 1.1 |

EXAMPLE 13

Preparation of H-NU-85

A portion of the product from Example 4 was calcined in air at 450° C. for 24 hours followed by 24 hours at 550° C. The resulting material was then contacted for 4 hours at 60° C. with a 1 molar solution of hydrochloric acid using 10 ml of solution per gram of solid calcined product. The material was then filtered, washed with deionised water and dried at 110° C.

Analysis for Na, Al and Si gave the following molar composition:

$$34.9SiO_2—Al_2O_3—0.001Na_2O$$

EXAMPLE 13A

Example 13 was repeated except the ion-exchange was carried out by contacting calcined material for 2 hours at ambient temperature with a 1 molar solution of hydrochloric acid, using 10 ml of solution per gram of solid calcined product. The ion-exchange procedure was repeated twice after which the material was filtered, washing with deionised water and dried at 110° C.

Analysis for Na, Al and Si gave the following molar composition:

$$32.0SiO_2—Al_2O_3—0.002Na_2O.$$

The sorptive capacity of this material for molecules of various sizes was measured. Table 10 contains the sorption results. Data for zeolite NU-87 for comparison purposes can be found in EP-A-377 291.

The data were obtained using a CI Robal Microbalance. Samples were calcined for 7 hours and evacuated for 2 hours at 550° C. before measurements were made. Results are presented as % (w/w) uptake at relative pressures (P/P$_o$), where P$_o$ is the saturated vapour pressure. The figures for apparent voidage filled were calculated assuming that the liquids maintain their normal densities at the sorption temperature.

EXAMPLE 14

Preparation of H-NU-85

A portion of the product from Example 5 was calcined in air at 450° C. for 24 hours followed by 24 hours at 550° C. The resulting material was then contacted for 2 hours at ambient temperature with a 1 molar solution of hydrochloric acid using 10 ml of solution per gram of solid calcined product. The material was then filtered, washed with deionised water, dried and the ion-exchange with hydrochloric acid repeated. Finally the material was filtered, washed with deionised water and then dried at 110° C.

Analysis for Na, Al and Si gave the following molar composition:

$$34.0SiO_2—Al_2O_3—0.001Na_2O$$

EXAMPLE 15

Preparation of H-NU-85

A portion of the product from Example 9 was calcined in air at 450° C. for 24 hours followed by 24 hours at 550° C. The resulting material was then contacted for 2 hours at ambient temperature with a 1 molar solution of hydrochloric acid using 10 ml of solution per gram of solid calcined product. The material was then filtered, washed with deionised water, dried and the ion-exchange with hydrochloric acid repeated. Finally the material was filtered, washed with deionised water and then dried at 110° C.

Analysis for Na, Al and Si gave the following molar composition:

$$30.9SiO_2—Al_2O_3—0.09Na_2O$$

EXAMPLE 16

Preparation of H-NU-85

A portion of the product from Example 10 was calcined in air at 450° C. for 24 hours followed by 24 hours at 550° C. The resulting material was then contacted for 4 hours at 60° C. with a 1 molar solution of hydrochloric acid using 10 ml of solution per gram of solid calcined product. The material was then filtered, washed with deionised water, dried and the ion-exchange with hydrochloric acid repeated. The resulting material was then calcined in air at 550° C. for 24 hours. Finally the material was filtered, washed with deionised water and then dried at 110° C.

Analysis for Na, Al and Si gave the following molar composition:

$25.5SiO_2$—$Al_2O_3$—$0.05Na_2O$

It is believed that the residual sodium in the sample is associated with the analcime and/or sodalite impurities.

EXAMPLE 16A

Example 16 was repeated except the final calcination was carried out at 550° C. for 16 hours. Analysis for Na, Al and Si by AAS gave the following molar composition:

$22.7SiO_2$—$Al_2O_3$—$0.05Na_2O$

EXAMPLE 16B

A portion of the product from Example 10 was discharged from the reactor and "worked-up" and activated separately from the remainder of the material. The product was filtered, washed with demineralised water and then dried at 110° C. The resulting material was calcined in air at 450° C. for 24 hours followed by 24 hours at 550° C. The resulting material was then contacted for 4 hours at 60° C. with a 1 molar solution of hydrochloric acid, using 10 ml of solution per gram of solid calcined product. The material was then filtered, washed with deionised water, dried and the ion-exchange with hydrochloric acid repeated. Finally the resulting material was calcined in air at 550° C. for 16 hours.

Analysis for Na, Al and Si gave the following molar composition:

$27.0SiO_2$—$Al_2O_3$—$0.04Na_2O$

EXAMPLE 17

Preparation of H-NU-85

A portion of the product from Example 12 was calcined in air at 450° C. for 24 hours followed by 24 hours at 550° C. The resulting material was then contacted for 4 hours at 60° C. with a 1 molar solution of hydrochloric acid using 10 ml of solution per gram of solid calcined product. The material was then filtered, washed with deionised water and dried at 110° C.

Analysis for Na, Al and Si gave the following molar composition:

$33.3SiO_2$—$Al_2O_3$—$<0.001Na_2O$

EXAMPLE 18

As stated above the preparation of NU-85 is sensitive to the silica to alumina ratio of reactants in the reaction mixture. This example demonstrates the relationship for a preparation carried out at 160° C.

A series of preparations were carried out using reaction mixtures with different silica/alumina ratios. Details of individual preparations are given in Tables 11 and 12.

All the preparations used "SYTON X30" as the source of silica and Sodium Aluminate (BDH Ltd) as the source of alumina. Reaction compositions, given in Tables 11 and 12, were calculated ignoring any sodium present in the "SYTON X30". Reaction mixtures were prepared as described in Example 9.

Figure 13:
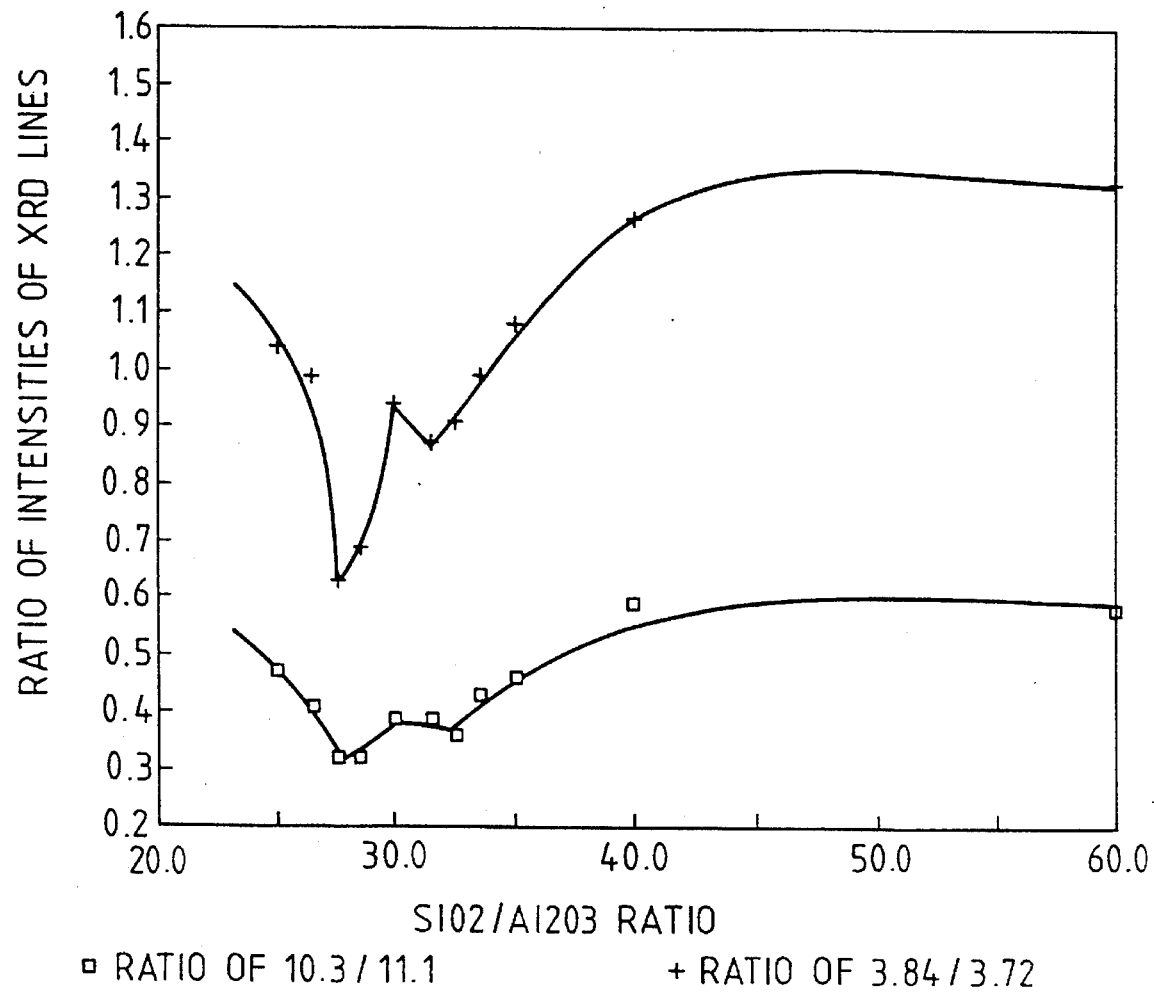
FIG. 13 is a plot of relative intensities of the 10.3 to 11.1 Å and 3.84 to 3.72 Å diagnostic X-ray lines of NU-85 versus $SiO_2/Al_2O_3$ ratio of a reaction mixture.

The products of each of the preparations were examined by X-ray powder diffraction. FIG. 13 is a plot of relative intensities of the 10.3 to 11.1 Å and 3.84 to 3.72 Å diagnostic x-ray lines of NU-85 versus the $SiO_2/Al_2O_3$ ratio of the reaction mixture. The ratio of the lines at 3.37 to 3.42 Å is not included in the plot because the presence of an Analcime impurity in some of the samples masks the true intensity of the line at 3.42 Å.

Examination of Table 11 and FIG. 13 shows as the aluminium content of the reaction mixture is increased, ie the $SiO_2/Al_2O_3$ ratio decreases the product has increased NU-85 character, ie the relative intensity of the line at 10.3 Å to the line at 11.1 Å and the relative intensity of the line at 3.84 Å to the line at 3.72 Å decreases.

However, at a $SiO_2/Al_2O_3$ ratio in the region of about 30 to 32 this trend is reversed and the NU-85 character of the product decreases. When the $SiO_2/Al_2O_3$ ratio is in the region of about 27 to 30 the amount of NU-85 character increases before again decreasing.

Without being bound by theory, it is believed the initial decrease in the amount of NU-85 character present in the product and, indeed, the overall "well-shaped" plot are associated with the preparation of an Analcime impurity. Analcime, being an aluminium-rich phase, is believed to act as "sink" for aluminium with the result that the reaction mixture has a higher effective $SiO_2/Al_2O_3$ ratio.

This example demonstrates that the preparation of NU-85 is critically dependant on the aluminium content of the reaction mixture. If either too much or too little aluminium is present EU-1 is formed in preference to NU-85.

EXAMPLE 19

A reaction mixture of molar composition $60SiO_2$—$2Al_2O_3$—$10Na_2O$—10 Hex $Br_2$—$3000H_2O$ $60SiO_2$—$2Al_2O_3$—$10Na_2O$—10 Hex $Br_2$—$3000H_2O$ 171.7 g "SYTON X30" (Monsanto: a colloidal silica sol containing 30% silica 7.488 g Sodium Aluminate (BDH Ltd: 27.85% w/w $Na_2O_3$ 38.90% w/w $Al_2O_3$, 33.25% w/w $H_2O$)

8.73 g Sodium Hydroxide 134.0 g $HexBr_2$ solution (Containing 38.6% w/w $HexBr_2$ in water)

565.1 g Water

The molar composition given does not include sodium present in the "SYTON X30"

The mixture was prepared as follows:

A—solution containing the sodium hydroxide and sodium aluminate in 250 g of water B—solution containing $HexBr_2$ in 150 g of water C—dispersion of "SYTON X30" in the remaining water.

Solution A was added to solution B and the resulting solution added, with stirring, to dispersion C. Stirring was continued until a smooth gel was obtained. The resulting mixture was transferred to a 1 litre stainless steel autoclave and reacted at 170° C., with stirring at 300 rpm using a pitched-paddle type impeller.

The preparation was sampled periodically after 144 hours at reaction temperature the preparation was crash cooled to ambient temperature and the product discharged. The product was filtered, washed with demineralised water and then dried at 110° C.

The product was analysed by X-ray powder diffraction and identifed as a highly crystalline sample of zeolite NU-85 containing no detectable crystalline impurities. The ratios of the intensities of the diagnostic XRD lines are:

| | Spacing/Å | Intensities | Ratio of intensities (rounded to one decimal place) |
|---|---|---|---|
| relationship (b) | 3.84 vs 3.72 | 30.15 vs 28.92 | 1.0 |
| relationship (a) | 10.3 vs 11.15 | 12.61 vs 25.63 | 0.5 |
| relationship (c) | 3.37 vs 3.42 | 21.36 vs 22.54 | 0.9 |

TABLE 2
X-RAY DATA FOR THE PRODUCT OF EXAMPLE 1

| d(Angstroms) | Relative Intensity |
|---|---|
| 21.02 | 3.7 |
| 11.25 | 26.3 |
| 10.21 | 18.1 |
| 9.82 | 5.4 |
| 6.90 | 2.8 |
| 5.80 | 3.5 |
| 5.64 | 3.0 |
| 4.90 | 1.2 |
| 4.66 | 37.2 |
| 4.34 | 100.0 |
| 4.11 | 8.8 |
| 4.02 | 55.5 |
| 3.83 | 30.1 |
| 3.72 | 22.4 |
| 3.65 | 3.0 |
| 3.60 | 1.9 |
| 3.50 | 2.5 |
| 3.44 | 14.8 |
| 3.36 | 19.1 |
| 3.28 | 37.4 |
| 3.16 | 4.9 |
| 3.09 | 5.1 |
| 3.01 | 1.6 |
| 2.95 | 6.6 |
| 2.90 | 1.8 |
| 2.70 | 4.8 |

TABLE 3
X-RAY DATA FOR THE PRODUCT OF EXAMPLE 2

| d(Angstroms) | Relative Intensity |
|---|---|
| 11.16 | 23.7 |
| 10.17 | 14.1 |
| 9.77 | 4.0 |
| 6.87 | 1.8 |
| 5.78 | 3.0 |
| 5.60 | 2.3 |
| 4.67 | 33.8 |
| 4.33 | 100.0 |
| 4.01 | 61.4 |
| 3.83 | 37.5 |
| 3.72 | 29.6 |
| 3.65 | 4.6 |
| 3.44 | 18.2 |
| 3.43 | 20.3 |
| 3.37 | 22.7 |
| 3.28 | 52.6 |
| 3.26 | 46.5 |
| 3.25 | 37.4 |

TABLE 3-continued
X-RAY DATA FOR THE PRODUCT OF EXAMPLE 2

| d(Angstroms) | Relative Intensity |
|---|---|
| 3.16 | 7.9 |
| 3.15 | 7.5 |
| 3.10 | 8.5 |
| 2.95 | 10.1 |
| 2.94 | 8.6 |
| 2.89 | 3.5 |
| 2.81 | 1.9 |
| 2.76 | 1.9 |
| 2.71 | 7.3 |
| 2.70 | 7.7 |

TABLE 4
X-RAY DATA FOR THE PRODUCT OF EXAMPLE 3

| d(Angstroms) | Relative Intensity |
|---|---|
| 11.16 | 31.5 |
| 10.24 | 12.2 |
| 6.88 | 2.1 |
| 5.78 | 2.4 |
| 5.59 | 3.0 |
| 4.67 | 33.3 |
| 4.64 | 26.0 |
| 4.33 | 100.0 |
| 4.02 | 58.3 |
| 3.85 | 22.6 |
| 3.83 | 20.3 |
| 3.72 | 23.0 |
| 3.43 | 19.3 |
| 3.37 | 20.9 |
| 3.29 | 47.0 |
| 3.29 | 54.8 |
| 3.26 | 37.1 |
| 3.16 | 4.8 |
| 3.10 | 5.9 |
| 2.95 | 5.1 |
| 2.71 | 4.5 |

TABLE 5
X-RAY DATA FOR THE PRODUCT OF EXAMPLE 4

| d(Angstroms) | Relative Intensity |
|---|---|
| 11.13 | 32.0 |
| 10.19 | 11.8 |
| 6.87 | 2.4 |
| 5.77 | 2.5 |
| 5.56 | 2.7 |
| 4.90 | 1.3 |
| 4.66 | 34.8 |
| 4.64 | 30.6 |
| 4.33 | 100.0 |
| 4.01 | 67.7 |
| 3.84 | 27.7 |
| 3.73 | 29.5 |
| 3.71 | 30.1 |
| 3.43 | 24.1 |
| 3.37 | 23.6 |
| 3.35 | 23.4 |
| 3.28 | 59.6 |
| 3.25 | 39.6 |
| 3.16 | 7.9 |
| 3.09 | 8.7 |
| 2.93 | 7.6 |
| 2.70 | 6.4 |

TABLE 6
X-RAY DATA FOR THE PRODUCT OF EXAMPLE 5

| d(Angstroms) | Relative Intensity |
|---|---|
| 11.09 | 27.6 |
| 10.16 | 13.5 |
| 10.08 | 12.5 |
| 6.85 | 2.2 |
| 5.74 | 2.7 |
| 5.57 | 2.3 |
| 4.66 | 33.3 |
| 4.32 | 100.0 |
| 4.01 | 63.2 |
| 3.84 | 32.2 |
| 3.82 | 28.9 |
| 3.72 | 30.6 |
| 3.44 | 20.4 |
| 3.43 | 22.1 |
| 3.36 | 23.7 |
| 3.27 | 57.4 |
| 3.15 | 7.7 |
| 3.10 | 8.8 |
| 2.94 | 8.9 |
| 2.80 | 1.7 |
| 2.70 | 6.8 |

TABLE 7
X-RAY DATA FOR THE PRODUCT OF EXAMPLE 6

| d(Angstroms) | Relative Intensity |
|---|---|
| 11.07 | 26.3 |
| 10.13 | 15.0 |
| 10.00 | 11.6 |
| 9.69 | 4.8 |
| 6.84 | 1.9 |
| 5.76 | 3.7 |
| 5.58 | 2.8 |
| 4.65 | 34.4 |
| 4.32 | 100.0 |
| 4.01 | 60.3 |
| 3.82 | 34.5 |
| 3.71 | 24.7 |
| 3.64 | 1.1 |
| 3.43 | 17.7 |
| 3.36 | 21.4 |
| 3.28 | 46.7 |
| 3.27 | 53.4 |
| 3.25 | 43.5 |
| 3.15 | 5.0 |
| 3.09 | 5.8 |
| 2.95 | 7.2 |
| 2.89 | 1.1 |
| 2.71 | 6.0 |

TABLE 8
X-RAY DATA FOR THE PRODUCT OF EXAMPLE 9

| d(Angstroms) | Relative Intensity |
|---|---|
| 11.20 | 33.2 |
| 10.39 | 10.5 |
| 6.89 | 2.5 |
| 5.58 | 13.1 |
| 4.67 | 34.6 |
| 4.34 | 100.0 |
| 4.02 | 71.8 |
| 3.89 | 20.0 |
| 3.85 | 20.0 |
| 3.73 | 31.9 |
| 3.72 | 23.4 |
| 3.42 | 37.4 |
| 3.37 | 23.5 |
| 3.28 | 64.1 |
| 3.26 | 44.8 |
| 3.17 | 6.1 |
| 3.10 | 8.7 |
| 2.91 | 13.1 |
| 2.71 | 5.6 |

TABLE 9
X-RAY DATA FOR THE PRODUCT OF EXAMPLE 10

| d(Angstroms) | Relative Intensity |
|---|---|
| 11.13 | 27.3 |
| 10.26 | 9.3 |
| 6.88 | 2.4 |
| 6.32 | 2.9 |
| 5.57 | 9.1 |
| 4.66 | 33.5 |
| 4.33 | 100.0 |
| 4.02 | 69.1 |
| 3.84 | 23.8 |
| 3.73 | 33.4 |
| 3.71 | 27.5 |
| 3.65 | 20.5 |
| 3.43 | 38.0 |
| 3.37 | 27.0 |
| 3.28 | 67.3 |
| 3.26 | 52.8 |
| 3.17 | 11.2 |
| 3.10 | 11.3 |
| 3.09 | 10.2 |
| 2.91 | 12.1 |
| 2.84 | 4.1 |
| 2.79 | 2.5 |
| 2.71 | 7.7 |

TABLE 10

SORPTION DATA FOR H-NU-85

| Sorbate | Adsorption Temperature [°C.] | Relative Pressure (P/P$_o$) | Uptake [%(w/w)] NU-85 | Apparent Voidage[1] filled [cm$^3$g$^{-1}$] NU-85 | Kinetic Diameter[2] A |
|---|---|---|---|---|---|
| n-Heptane | 20 | 0.13 | 0.073 | 0.11 | 4.3 |
|  |  | 0.31 | 0.082 | 0.12 |  |
|  |  | 0.52 | 0.096 | 0.14 |  |
| Toluene | 20 | 0.11 | 0.081 | 0.09 | 5.85 |
|  |  | 0.32 | 0.098 | 0.11 |  |
|  |  | 0.48 | 0.109 | 0.13 |  |
| Cyclohexane | 20 | 0.12 | 0.043 | 0.06 | 6.0 |
|  |  | 0.37 | 0.053 | 0.07 |  |
|  |  | 0.49 | 0.058 | 0.07 |  |

[1]The apparent voidage filled was calculated assuming the liquids maintain their normal densities at the adsorption temperature.
[2]Kinetic diameters are taken from "Zeolite Molecular Sieves", D W Breck, J Wiley and Sons, 1976 p636. The value for toluene was assumed to be the same as for benzene, and n-heptane the same as n-butane
[3]The uptake is grams of sorbate per 100 grams of anhydrous zeolite.

TABLE 11

Products obtained from reaction mixtures of composition:
60 SiO$_2$ - X Al$_2$O$_3$ - 10 Na$_2$O - 10 HexBr$_2$ - 3000 H$_2$O
All synthesis were carried out at 160° C. in stirred,
1 or 2 liter, stainless steel autoclaves.

| Example | X | SiO$_2$/Al$_2$O$_3$ | t/h | Ratio of XRD lines 10.3/11.1 | 3.84/3.72 | % w/w Analcime |
|---|---|---|---|---|---|---|
| A | 2.4 | 25 | 333 | 0.5 | 1.0 | 16.2 |
| B | 2.264 | 26.5 | 383 | 0.4 | 1.0 | 10.6 |
| C* | 2.18 | 27.5 | 450 | 0.3 | 0.6 | 4.7 |
| D | 2.105 | 28.5 | 432 | 0.3 | 0.7 | 3 |
| E | 2 | 30 | 449 | 0.4 | 0.9 | 4.4 |
| F | 1.905 | 31.5 | 316 | 0.4 | 0.9 | 0.7 |
| G | 1.846 | 32.5 | 312 | 0.4 | 0.9 | 0.2 |
| H | 1.791 | 33.5 | 263 | 0.4 | 1.0 | 0.7 |
| I | 1.714 | 35 | 264 | 0.5 | 1.1 | 0 |
| J** | 1.5 | 40 | 240 | 0.6 | 1.3 | 0 |
| K | 1 | 60 | 142 | 0.6 | 1.3 | 0 |

*Example 9
**Example 2

TABLE 12

NU-85 Preparation: 1 and 2 liter autoclaves

| Composition[1] | Reagents[2] | Temp | Time | % Analcime |
|---|---|---|---|---|
| 60, 1.000, 10, 10, 3000 | SiO$_2$, SA, Soln | 160 | 142 | 0 |
| 60, 1.500, 10, 10, 3000 | SiO$_2$, SA, Soln | 160 | 240 | 0 |
| 60, 1.714, 10, 10, 3000 | SiO$_2$, SA | 160 | 264 | 0 |
| 60, 1.791, 10, 10, 3000 | SiO$_2$, SA, Soln | 160 | 263 | 0.7 |
| 60, 1.846, 10, 10, 3000 | SiO$_2$, SA, Soln | 160 | 312 | 0.2 |
| 60, 1.905, 10, 10, 3000 | SiO$_2$, SA, Soln | 160 | 316 | 0.7 |
| 60, 2.000, 10, 10, 3000 | SiO$_2$, SA | 160 | 449 | 4.4 |
| 60, 2.105, 10, 10, 3000 | SiO$_2$, SA, Soln | 160 | 432 | 3 |
| 60, 2.180, 10, 10, 3000 | SiO$_2$, SA, Soln | 160 | 450 | 4.7 |
| 60, 2.264, 10, 10, 3000 | SiO$_2$, SA, Soln | 160 | 383 | 10.6 |
| 60, 2.4, 10, 10, 3000 | SiO$_2$, SA | 160 | 333 | 16.2 |

Notes:
[1]Composition = SiO$_2$, Al$_2$O$_3$, Na$_2$O, HexBr$_2$, H$_2$O
[2]Reagents: SiO$_2$ = "SYTON X30" (BDH); SA = Sodium Aluminate (BDH); Soln = HexBr$_2$ solution otherwise solid HexBr$_2$ was used The invention also provides a catalyst composition comprising zeolite NU-85 and catalytic processes employing zeolite NU-85 as a catalyst.

In the catalysts according to the invention XO$_2$ is preferably silica and Y$_2$O$_3$ is preferably alumina. Such catalysts may be used in a wide variety of catalytic processes and using a wide variety of feedstocks.

Catalytically useful forms of zeolite NU-85 include the hydrogen and ammonium forms, prepared by the methods hereinbefore described.

Catalysts according to the invention comprising NU-85 may also comprise one or more elements, especially metals or cations thereof, or compounds of said elements, especially metal oxides. Such catalysts may be prepared by ion-exchange or impregnation of zeolite NU-85 with the said element, cation or compound, or a suitable precursor of said cation or compound. Such ion-exchange or impregnation may be carried out on the "as-prepared" zeolite NU-85, the calcined form, the hydrogen form and/or the ammonium form and/or any other exchanged form.

In cases where a metal-containing form of zeolite NU-85 is prepared by ion-exchange it may be desirable to effect complete exchange of the metal, by which is meant that substantially all of the exchangeable sites are occupied by the metal. Such forms may be particularly useful in separation process, for example the separation of xylenes. In most cases, however, it is preferable to effect only partial exchange of the metal, the remaining sites being occupied by another cation especially hydrogen or ammonium cations. In some cases it may be desirable to introduce two or more metal cations by ion exchange.

In cases where zeolite NU-85 is impregnated with a metal compound to form a catalyst, the metal compound may be added in any suitable quantity, but 20% by weight is generally sufficient for most applications; for some applications up to 10% by weight is sufficient, and quantities of up to 5% are often appropriate. Impregnation may be carried by any suitable method known in the art of catalyst preparation.

Metal-exchanged forms or forms in which a metal compound has been impregnated may be used as such or they may be treated to produce an active derivative. Treatments include reduction, for example in an atmosphere comprising hydrogen, to produce a metal or other reduced forms. Such treatments may be carried out at a suitable stage in the catalyst preparation or may conveniently be carried out in the catalytic reactor.

Catalytic compositions comprising zeolite NU-85 can, if desired, be associated with an inorganic matrix which may be either inert or catalytically active. The matrix may be present solely as a binding agent to hold the zeolite particles together, possibly in a particular shape or form, for example as a pellet or extrudate, or it may function as an inert diluent, for example to control the activity per unit weight of catalyst. When the inorganic matrix or diluent is itself catalytically active it can thereby form an effective part of the zeolite/matrix catalyst composition. Suitable inorganic matrices and diluents include conventional catalyst support materials such as silica, the various forms of alumina, clays such as bentonites, montmorillonites, sepiolite, attapulgite, Fullers Earth and synthetic porous materials such as silica-alumina, silica-zirconia, silica-thoria, silica-beryllia or silica-titania. Combinations of matrices are contemplated within the present invention, especially combinations of inert and catalytically-active matrices.

When zeolite NU-85 is associated with an inorganic matrix material or a plurality thereof, the proportion of matrix material or materials in the total composition usually amounts to up to about 90% by weight, preferably up to 50% by weight, more preferably up to 30% by weight.

For some applications another zeolite or molecular sieve may be used in conjunction with zeolite NU-85 to form a catalyst. Such a combination may be used as such or associated with one or more matrix materials hereinbefore described. A particular example of the use of such an overall composition is as a fluid catalytic cracking catalyst additive, in which case zeolite NU-85 is preferably used in an amount of 0.5 to 5% by weight of the total catalyst.

For other applications zeolite NU-85 may be combined with another catalyst, such as platinum on alumina.

Any convenient method of mixing zeolite NU-85 with an inorganic matrix and/or another zeolite material, may be employed, especially that suited to the final form in which the catalyst is used, for example extrudates, pellets or granules.

If zeolite NU-85 is used to form a catalyst in conjunction with a metal component (for example, a hydrogenation/ dehydrogenation component or other catalytically active metal) in addition to an inorganic matrix, the metal component can be exchanged or impregnated into the zeolite NU-85 itself before addition of the matrix material or into the zeolite-matrix composition. For some applications it may be advantageous to add the metal component to the whole or part of the matrix material before mixing the latter with the zeolite NU-85.

A wide range of hydrocarbon conversion catalysts comprising zeolite NU-85 can be prepared by ion-exchange or impregnation of the zeolite with one or more cations or oxides derived from elements selected from Cu, Ag, Ga, Mg, Ca, Sr, Zn, Cd, B, Al, Sn, Pb, V, P, Sb, Cr, Mo, W, Mn, Re, Fe, Co, Ni and noble metals.

In cases where catalysts comprising zeolite NU-85 contain one or more hydrogenation/dehydrogenation components such as the metals Ni, Co, Pt, Pd, Re and Rh, such components can be introduced by ion-exchange or impregnation of a suitable compound of the metal.

Catalyst compositions comprising zeolite NU-85 may find application in reactions involving saturated and unsaturated aliphatic hydrocarbons, aromatic hydrocarbons, oxygenated organic compounds and organic compounds containing nitrogen and/or sulphur as well as organic compounds containing other functional groups.

In general, catalyst compositions comprising zeolite NU-85 can be usefully employed in reactions involving isomerisation, transalkylation and disproportionation, alkylation and de-alkylation, dehydration and hydration, oligomerisation and polymerisation, cyclisation, aromatisation, cracking, hydrogenation and dehydrogenation, oxidation, halogenation, synthesis of amines, hydrodesulphurisation and hydrodenitrification, ether formation and synthesis of organic compounds in general.

The above processes may be carried out in either the liquid or vapour phase under conditions which are chosen as suitable for each individual reaction. For example, the reactions carried out in the vapour phase may involve the use of fluid bed, fixed bed or moving bed operations. Process diluents may be used when required. Depending upon the particular process, suitable diluents include inert gases (such as nitrogen or helium), hydrocarbons, carbon dioxide, water or hydrogen. The diluent may be inert or it may exert a chemical effect. It may be an advantage, especially in cases where hydrogen is used, to include a metal component, such as a hydrogenation/dehydrogenation component, for example one or more of the metals, Ni, Co, Pt, Pd, Re or Rh as part of the catalyst composition.

According to a further aspect of the present invention we provide a hydrocarbon conversion process which comprises contacting an alkylbenzene or a mixture of alkylbenzenes under isomerisation conditions in the vapour or liquid phase with a catalyst comprising zeolite NU-85.

Isomerisation reactions for which catalysts comprising zeolite NU-85 are of particular use are those involving alkanes and substituted aromatic molecules, especially xylenes. Such reactions may include those which can be carried out in the presence of hydrogen. Catalyst compositions containing zeolite NU-85 which are of particular use in isomerisation reactions include those in which the NU-85 is in its acid (H) form, cation-exchanged form, or other metal-containing forms or combinations thereof. Especially useful are those forms in which the metal is a hydrogenation/ dehydrogenation component such as Ni, Co, Pt, Pd, Re or Rh.

Particular isomerisation reactions in which a catalyst comprising NU-85 may be found useful include xylene isomerisation and hydroisomerisation of xylenes, paraffin, in particular $C_4$ to $C_{10}$ normal hydrocarbons, or olefin isomerisation and catalytic dewaxing.

Xylene isomerisation and hydroisomerisation may be carried out in the liquid or vapour phase. In the liquid phase, suitable isomerisation conditions include a temperature in the range 0°–350° C., a pressure in the range 1–200 atmospheres absolute, preferably 5–70 atmospheres absolute, and when conducted in a flow system, a weight hourly space velocity (WHSV) preferably in the range 1–30 hr$^{-1}$ based on the total catalyst composition. Optionally, a diluent may be present, suitably one or more of those having a critical temperature higher than the isomerisation conditions being used. The diluent, if present, may comprise 1–90% by weight of the feed. Vapour phase xylene isomerisation and hydroisomerisation reactions are most suitably carried out at a temperature in the range 100°–600° C., preferably 200°–500° C., at a pressure in the range 0.5–100 atmosphere absolute, preferably 1–50 atmospheres absolute, and at a WHSV up to 80 based on the total catalyst composition.

When xylene isomerisation is conducted in the presence of hydrogen (in the vapour phase), the preferred hydrogenation/dehydrogenation component is Pt or Ni. The hydrogenation/dehydrogenation component is usually added in an amount of between 0.05 and 2% by weight of the total catalyst. Additional metals and/or metal oxides may be present in the catalyst composition.

In xylene isomerisation, ethylbenzene may be present in the xylene feed in amounts up to 40% by weight. Over catalyst compositions comprising zeolite NU-85 the ethylbenzene will undergo transalkylation with itself, and with xylenes, to form heavier and lighter aromatic compounds. The ethylbenzene will also react to form benzene and light gas, particularly at temperatures above 400° C. With such xylene feeds containing ethylbenzene, when reaction is carried out in the presence of hydrogen over a catalyst composition comprising zeolite NU-85 together with a hydrogenation/dehydrogenation component, some of the ethylbenzene will isomerise to xylenes. It may also be an advantage to carry out xylene isomerisation reactions in the presence of a hydrocarbon compound, especially a paraffin or naphthene with or without the additional presence of hydrogen. The hydrocarbon appears to improve catalyst performance in that reactions which lead to xylenes loss are suppressed and, particularly when reactions are carried out in the absence of hydrogen, catalyst life is extended.

According to yet a further aspect of the present invention we provide a hydrocarbon conversion process which comprises contacting one or more alkylated aromatic compounds under transalkylation conditions in the vapour or liquid phase with a catalyst comprising zeolite NU-85.

Catalysts comprising zeolite NU-85 are of especial value in transalkylation and disproportionation reactions, in particular those reactions involving mono-, di-, tri- and tetra-alkyl substituted aromatic molecules, especially toluene and xylenes.

Catalyst compositions comprising NU-85 which are of particular use in transalkylation and disproportionation reaction include those in which the NU-85 component is in its acid (H) form, its cation-exchanged form, or other metal-containing forms or combinations thereof. Especially useful is the acid form and those forms in which the metal is a hydrogenation/dehydrogenation component such as Ni, Co, Pt, Pd, Re or Rh.

Particular examples of important processes include toluene disproportionation and the reaction of toluene with aromatic compounds containing 9 carbon atoms, for example trimethyl benzenes.

Toluene disproportionation can be conducted in the vapour phase either in the presence or absence of hydrogen, although the presence of hydrogen is preferred as this helps to suppress catalyst deactivation. The most suitable reaction conditions are: temperatures in the range 250°–650° C., preferably 300°–550° C.; pressures in the range 0.3–100 atmospheres absolute, preferably 1–50 atmospheres absolute; weight hourly space velocity up to 50 (based on the total catalyst composition).

When toluene disproportionation is conducted in the presence of hydrogen the catalyst may, optionally, contain a hydrogenation/dehydrogenation component. The preferred hydrogenation/dehydrogenation component is Pt, Pd, or Ni. The hydrogenation/dehydrogenation component is normally added in a concentration of up to 5% by weight of the total catalyst composition. Additional metals and/or metal oxides may be present in the catalyst composition, for example up to 5% by weight of the total catalyst, composition.

The present invention further provides a hydrocarbon conversion process which comprises reacting an olefinic or aromatic compound with a suitable alkylating compound under alkylating conditions in the vapour or liquid phase over a catalyst comprising zeolite NU-85.

Among the alkylation reactions for which catalysts comprising zeolite NU-85 are of particular use are the alkylation of benzene or substituted aromatic molecules with methanol or an olefin or ether. Specific examples of such processes include toluene methylation, ethylbenzene synthesis, and the formation of ethyl toluene and cumene. Alkylation catalysts used in processes according to this further aspect of the invention my comprise further materials, especially metal oxides which may improve catalytic performance.

Catalysts comprising zeolite NU-85 may find application in reactions involving the dehydration of alcohols, for example methanol and higher alcohols, to form hydrocarbons, including olefins and gasoline. Other feedstocks for dehydration reactions involving a catalyst comprising NU-85 include ethers, aldehydes and ketones.

By the use of a catalyst comprising NU-85, hydrocarbons can be generated by carrying out oligomerisation, cyclisation and/or aromatisation reactions on unsaturated compounds such as ethene, propene or butene, on saturated compounds such as propane or butane or mixtures of hydrocarbons such as light naphthas. For some reactions, particularly aromatisation reactions, the catalyst may usefully comprise a metal or metal oxide, especially platinum, gallium, zinc or their oxides.

Catalysts comprising NU-85 are of use in a variety of cracking reactions, including the cracking of olefins, paraffins or aromatics or mixtures thereof. Of particular value is the use of zeolite NU-85 as a fluid catalytic cracking catalyst additive to improve the product of the cracking reaction. Zeolite NU-85 may also be used as a component of a catalyst in catalytic dewaxing or hydrocracking processes.

Hydrogenation/dehydrogenation processes, for example the dehydrogenation of alkanes to the corresponding olefins, are suitably carried out by contacting the appropriate feedstock under appropriate conditions with a catalyst comprising zeolite NU-85, especially when the latter also comprises a hydrogenation/dehydrogenation component such as Ni, Co, Pt, Pd, Re or Ru.

Zeolite NU-85 is useful as a component in a catalyst for the preparation of amines, for example the production of methylamines from methanol and ammonia.

Zeolite NU-85 is also a useful catalyst for the formation of ethers, particularly by the reaction of two alcohols or by the reaction of an olefin with an alcohol.

The invention relating to catalysts comprising NU-85 and processes using these catalysts is illustrated by the following Examples.

EXAMPLE 20

Disproportionation of Toluene

A portion of the product from Example 13 was compacted into aggregates of a size within the range 425 and 1000 microns. 1 g of this material was placed in a 4 mm internal diameter stainless steel reactor and calcined at 500° C. in air for 16 hours at atmospheric pressure. The air was replaced by nitrogen and the reactor and contents were cooled to 350° C. Hydrogen was then passed through the reactor and the pressure raised to 2069 kPa. The hydrogen flow rate was set at 1728 cm³ per hour as measured at atmospheric pressure. After 1 hour, toluene was introduced into the hydrogen stream at a rate of 1.9 ml of liquid per hour. The mole ratio of hydrogen to toluene was 4 to 1 and the weight of toluene per unit weight of solid was 1.64. The reaction was continued for 7 days during which the temperature was increased stepwise in order to maintain 47% conversion of the toluene.

This procedure was repeated with a portion of material from Examples 14, 15 and 16B. (* A portion of the final product from Example 12 was activated by a procedure similar to that described in Example 17 and also tested.) The composition of the product from the tests after a reaction time of 150 hours is given below in Table 13.

TABLE 13

| Ex- ample | Temp °C. | Wt % products at 47% conversion | | | | |
|---|---|---|---|---|---|---|
| | | Gas | Benzene | Ethyl-Benzene | Xylenes | C₉ Aromatics |
| 13 | 382 | 0.2 | 19.9 | 0.1 | 23.8 | 3.2 |
| 14 | 409 | 0.3 | 20.4 | 0.2 | 22.9 | 3.2 |
| 15 | 359 | 0.1 | 19.5 | 0.1 | 24.2 | 3.1 |
| 16B | 366 | 0.2 | 19.9 | 0.1 | 23.5 | 3.0 |
| 12* | 390 | 0.8 | 20.2 | 0.2 | 22.7 | 3.1 |

The results in Table 13 show that the three samples tested have different activites in toluene disproportionation as indicated by the temperature required to give 47% conversion.

Figure 14:
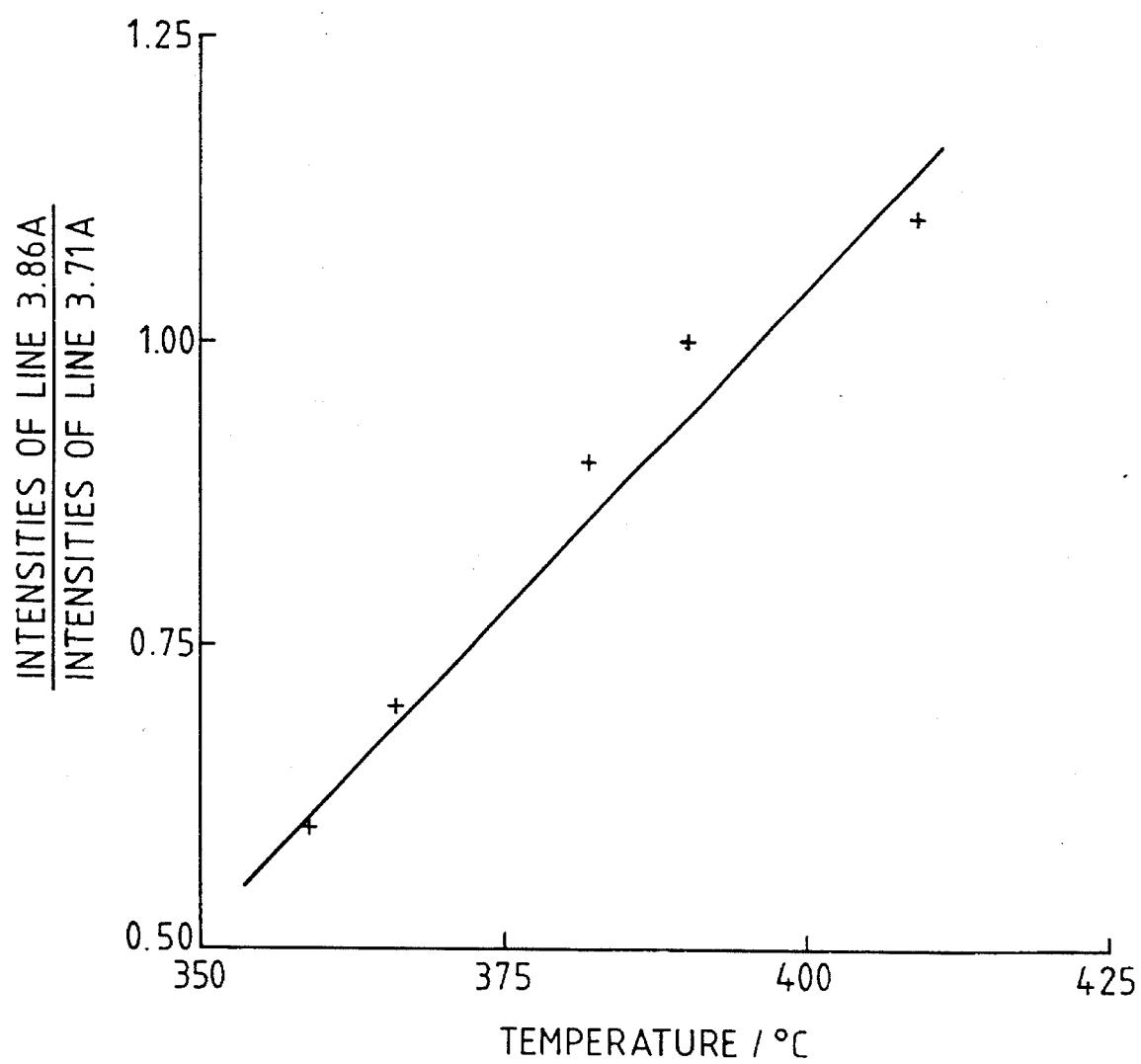
FIG. 14 compares the activity of several zeolite NU-85 samples in disproportionation.

Table 14 and FIG. 14 compare the activity of the above samples of zeolite NU-85 in toluene disproportionation, as measured by the temperature required to give 47% conversion, against the ratio of the intensity of the XRD line at 3.86± 0.08 Å to the intensity of the line at 3.71 ±0.07 Å.

TABLE 14

| Example | Intensity of the lines/A | | Ratio of intensity of lines 3.86 to 3.7 (to one decimal place) | Temp required to give 47% conversion /°C. |
|---|---|---|---|---|
| | 3.86 ± 0.08 | 3.71 ± 0.07 | | |
| 13 | 27.7 | 30.1 | 0.9 | 382 |
| 14 | 32.2 | 30.6 | 1.1 | 409 |
| 15 | 20.0 | 31.9 | 0.6 | 359 |
| 16B | 23.8 | 33.4 | 0.7 | 366 |
| 12* | 29.9 | 29.0 | 1.0 | 290 |

The linear nature of the plot illustrates that there is a direct relationship between the catalytic performance of zeolite NU-85 and relative intensities of characteristic lines in the XRD of the samples. This provides further evidence that zeolite NU-85 is a family of materials.

EXAMPLE 21

Cracking of n-butane

The cracking of n-butane over H-NU-85 was examined using a portion of the material from Example 16. The procedure followed that described by: H. Rastelli Jr., B. M. Lok, J. A. Duisman, D. E. Earls and J. T. Mullhaupt, Canadian Journal of Chemical Engineering, Volume 60, February 1982, pages 44–49, the contents of which are incorporated herein by reference.

A portion of the product from Example 16 was pelleted, broken down and sieved to give a 500–1000 micron size fraction. 0.268 g of this material was charged to a stainless-steel micro reactor (internal diameter 4.6 mm) and supported on glass wool and glass balls. The material was then dehydrated "in situ" by heating at 500° C. for 5.5 hours in a stream of dry nitrogen.

A feed containing 2.19% v/v n-butane, 15.36% v/v nitrogen and 82.45% v/v helium was passed over the catalyst bed. The catalyst bed was maintained at a temperature of 500° C. and atmospheric pressure. The cracked products were analysed by gas chromatography. This showed that the zeolite cracked n-butane to $C_1$–$C_3$ hydrocarbons. At a feed flow rate of 50.0 cm³ per minute an n-butane conversion of 37.0% was measured. This corresponds to a $k_A$ of 85 cm³/g min using the equation given in the above reference.

The zeolite was then regenerated by heating at 500° C. for 5 hours in a stream of air. The feed was reintroduced at a feed flow rate of 49.6 cm³ per minute and a n-butane conversion of 32% was measured. This corresponds to a $k_A$ of 72 cm³/g min.

This example shows that zeolite NU-85 is an active catalyst for n-butane cracking.

EXAMPLE 22

Fluid Catalytic Cracking Additive

Zeolite NU-85 was evaluated as a fluid catalytic cracking (FCC) additive by adding it in small quantities to a base FCC catalyst and then monitoring its effect on the cracking products in a microactivity test (MAT) run.

Base Catalyst

The base FCC catalyst used was Resoc-1 E-Cat (Grace Davidson). The "E-Cat" indicates that the catalyst has been deactivated on line in a FCC plant. The base catalyst was decoked by calcining in air for 24 hours at 550° C. Resoc-1 is a rare earth exchanged Ultrastabilised Y zeolite based catalyst in spray dried form.

Additive Catalyst

The sample of NU-85 was tested by preparing a catalyst comprising Resoc-1, E-Cat+1% by weight fresh NU-85 based on the weight of Resoc-1, E-Cat. (The % weight of NU-85 was based on anhydrous material)

Individual catalysts were prepared by thorough physical mixing of the base catalyst with a portion of material from Example 16. The mixture was then compressed. The resulting pellet was broken up and sieved to give granules with a size in the range of 44 to 70 microns.

The feedstock used in these experiments was Cincinnati gas oil. The properties of this material are as follows.

| Vacuum Distillation | °C. |
|---|---|
| 10% at 760 mm | 312.7 (595° F.) |
| 30% | 362.8 (685° F.) |
| 50% | 407.2 (765° F.) |
| 70% | 451.7 (845° F.) |
| 80% | 501.1 (934° F.) |

The MAT runs were carried out in a fixed bed unit using a 0.897 g charge of Cincinnati gas oil and 2.5 g of catalyst. The contact time was 80 seconds. The weight hourly space velocity (WHSV) of individual runs is given in Table 15.

The catalyst samples had all been calcined in air at 538° C. (1000° F.) for 1 hour before testing. The starting temperature for each run was 515.6° C. (960° F.).

The products were analysed by gas chromatography capillary column analysis from which the research octane number (RON) of the resulting gasoline could be determined. Table 15 lists this data.

From results given in Table 15 it can be seen that the addition of zeolite NU-85 increased the yield of $C_3$ and $C_4$ paraffins and olefins, although this is at the expense of a reduced gasoline yield. The overall FCC gasoline and alkylate yield was essentially unchanged. The zeolite NU-85 addititve increased the RON of the gasoline by two points. Analysis of the gasoline showed that this was mainly due to an increased concentration of the $C_6$ to $C_8$ aromatics (benzene, toluene, ethylbenzene and xylenes).

EXAMPLE 23

Hydroisomerisation of n-Pentane

A slurry consisting of 20.20 g of the material from Example 16, 8.30 ml of a chloroplatinic acid solution and 50 ml of deionised water was stirred in a closed vessel at room temperature for 4 hours. (The chloroplatinic acid solution contained the equivalent of 0.340 g of platinum in 25 ml of deionised water). Water was then evaporated from the mixture using a rotary evaporator and the resultant solid calcined in air at 500° C. for 3 hours.

The platinum impregnated zeolite powder thus produced was analysed by Atomic Adsorption Spectroscopy (AAS) and found to contain 0.41 weight per cent platinum. The powder was pelleted, broken-down and sieved to give a 500 to 1000 micron size fraction.

1.16 g of this material was transferred to a stainless steel reactor (internal diameter 4.2 mm) and reduced under a stream of hydrogen at 250° C. and a pressure of 420 psig for 19 hours. Liquid n-pentane, which had previously been dried over a molecular sieve, was vaporised and mixed with hydrogen gas to produce a mixture with a molar ratio of $H_2$ to pentane of 1.6:1. This mixture was passed over the catalyst bed at a weight hourly space velocity (WHSV) of 0.9 hour$^{-1}$ (based on the n-pentane) at a pressure of 437 psig and a temperature of 251° C. The product leaving the reactor bed was analysed by on line chromatography. It was found to contain 61% isopentane and 39% n-pentane. This corresponds to a conversion of 61%.

Since the maximum conversion possible at 251° C. is 72%, ie the limiting thermodynamic equilibrium mixture of n-and iso-pentane,the high conversion achieved with the Pt-NU-85 catalyst demonstrates its high activity in n-pentane hydroisomerisation.

EXAMPLE 24

Preparation of Amines

A portion of material from Example 16 was pelleted, broken down and sieved to give a 500–1000 micron size fraction. A sample of this material (2.91 g) was charged to a tubular stainless steel microreactor and heated to 180° C. under a flow of nitrogen before ammonia was introduced. After further heating to 300° C., methanol was introduced and conditions were adjusted to give the desired methanol conversion. The reaction products were measured by on-line gas chromatography and found to consist of a mixture of mono-, di- and tri-methylamines. After two days on stream, at a temperature of 330° C. and using a feed containing a molar ratio of ammonia to methanol of 2 at a gas hourly space velocity (GHSV) of 1100 hr$^{-1}$ the methanol conversion was 99% and the product consisted of 38 mole% monomethylamine, 26 mole % dimethylamine and 36 mole % trimethylamine.

This example demonstrates the use of zeolite NU-85 as a catalyst for the preparation of amines.

EXAMPLE 25

Isomerisation of Xylenes

A portion of the material from Example 16A was pelleted, broken down and sieved to give aggregates of between 425 and 1000 microns in size. 0.5 g of the aggregates were placed in a 5 mm internal diameter stainless steel tubular reactor and calcined in air for 16 hours at 500° C. and at atmospheric pressure. The air was purged with nitrogen and the reactor and contents were cooled to 300° C.

A mixture of C8 aromatic hydrocarbons was pumped into a vaporiser and then through the reactor at 300° C. and atmospheric pressure. The rate was initially 10 ml of liquid per hour. The product was analysed regularly. After 24 hours the temperature was increased to 360° C. and the feed rate reduced to 5.0 ml per hour. As the conversion fell, the temperature was further increased.

The feed and product compositions obtained are given in Table 16.

The results show that NU-85 catalyses the isomerisation of xylenes with only small xylenes losses, particularly at temperatures above 400° C. Ethylbenzene loss, which is desirable for efficient xylenes isomerisation plant operation, was quite high.

EXAMPLE 26

Methylation of Toluene

The sample of zeolite NU-85 (0.5 g) used in the previous example and still in the tubular reactor was calcined in air at 500° C. for 16 hours. The reactor was then purged with nitrogen as it was cooled to 300° C.

A mixture of toluene and methanol, in a mole ratio of 3 to 1, was pumped through the reactor at a temperature of 300° C. and atmospheric pressure.

The composition of the aromatic compounds in the product at various times is given in Table 17.

EXAMPLE 27

Ethylation of Benzene

The sample of zeolite NU-85 (0.5 g) used in the previous example and still in the tubular reactor was calcined in air at 500° C. for 16 hours. The reactor was then purged with nitrogen and cooled to 350° C.

A mixture of benzene and ethylene, in a mole ratio of 3 to 1, was pumped through the reactor at 300° C. and 20 Bar pressure.

The composition of the product at various times and temperatures is given in Table 18.

It is clear from the results that overall selectivity to ethylbenzene is high. No xylenes, which would be difficult to remove from the product, were detected.

EXAMPLE 28

Hydroisomerisation of Xylenes

A sample of the material from Example 16A was pelleted, broken down and sieved to give aggregates of between 425 and 1000 microns in size. 0.1 g of the aggregates were placed in a 3 mm internal diameter stainless steel reactor and calcined in air for 16 hours at 500° C. and atmospheric pressure. The air was purged with nitrogen and the reactor and contents cooled to 330° C. Hydrogen was then introduced into the reactor and the pressure allowed to increase to 6.7 bar. The flow of hydrogen through the reactor was then set at 4.52 litres per hour.

A mixture of $C_8$ aromatic hydrocarbons was added to the hydrogen stream at a rate of 5.70 ml of liquid per hour. (The mole ratio of hydrogen to hydrocarbon was 4 to 1.) The product was analysed regularly. The temperature was increased stepwise as the conversion fell.

At the end of the test the hydrocarbon feed rate had doubled whilst the hydrogen feed-rate remained unchanged.

The feed and product compositions are given in Table 19.

EXAMPLE 29

Propane Aromatisation 1.73 g of the material from Example 16 was stirred with 16 ml of a $7 \times 10^{-3}$ M solution of $Ga(NO_3)_3$ at 80° C. for 3 hours. Water was removed by rotary evaporation. The resulting powder was analysed by AAS and found to contain 0.4% by weight of gallium. The powder was pelleted, broken down and sieved to give a 500 to 1000 micron size fraction. 0.45 g of this fraction was then calcined in a stainless steel tubular reactor, under a stream of dry air, at a rate of 1.5 litres per hour, at 532° C. for 3 hours.

A feed of propane gas in nitrogen (29% propane) was passed over the calcined material at a pressure of 1.5 psig propane and a weight hourly space velocity of 1.95 $hr^{-1}$. The temperature was 532° C. The resulting gaseous products were analysed by gas chromatography. A gas analysis after 13 minutes on line at reaction temperature showed that 21% of the propane feed had been converted. In the gaseous hydrocarbon products, the concentration of benzene was 14.5 wt %, of toluene 14.5 wt %, and of xylene isomers 1 wt %. Therefore, the total concentration of aromtics in the gaseous hydrocarbon products was 30 wt %.

This example demonstrates the use of a gallium impregnated zeolite NU-85 in the aromatisation of propane.

TABLE 15

Fluid Catalytic Cracking Additive

| Catalyst | | (Comparative) Resoc-1, E-CAT | |
|---|---|---|---|
| WHSV ($hr^{-1}$) | | 15.74 | 15.98 |
| Temperature | Starting | 515.6° C. | 515.6° C. |
| | lowest | 501.1° C. | 495.6° C. |
| | | Wt % | Wt % |
| Conversion | | 63.23 | 65.45 |
| Product Yields | | | |
| Total C3's | | 4.44 | 6.00 |
| Propane | | 0.84 | 1.29 |
| Propylene | | 3.60 | 4.71 |
| Total C4's | | 8.40 | 11.02 |
| I-Butane | | 3.45 | 4.83 |
| N-Butane | | 0.67 | 0.80 |
| Total Butenes | | 4.29 | 5.38 |
| 1-Butene | | 2.01 | 2.78 |
| Trans-Butenes | | 1.31 | 1.50 |
| Cis-Butenes | | 0.96 | 1.10 |
| BP range $C_5$- 430° F. Gasoline | | 44.11 | 40.76 |
| BP range 430– 650° F. Light Cycle Gas Oil | | 22.43 | 21.04 |
| BP range 650° F. and above Diesel Oil | | 14.34 | 13.51 |
| FCC Gasoline + Alkylate (VOL %) | | 76.83 | 78.86 |
| Research Octane Number (Gasoline) | | 93.3 | 95.3 |

BP= Boiling point

TABLE 16

Isomerisation of Xylenes over NU-85

| | feed | product composition (wt %) | | | |
|---|---|---|---|---|---|
| Time (hr) | | 10 | 71 | 96 | 151 |
| Temperature (°C.) | | 300 | 330 | 360 | 400 |
| Feed Rate (ml/h) | | 10.0 | 5.0 | | |
| Gas (wt %) | | 0.01 | 0.00 | 0.00 | 0.01 |
| Benzene (wt %) | 0.17 | 0.37 | 0.38 | 0.26 | 0.27 |
| Toluene (wt %) | 1.03 | 5.47 | 6.76 | 2.58 | 2.22 |
| Non Arom (wt %) | 0.08 | 0.08 | 0.08 | 0.08 | 0.08 |
| E Benzene (wt %) | 3.96 | 2.77 | 2.50 | 3.52 | 3.61 |
| P Xylene (wt %) | 11.89 | 18.85 | 19.11 | 20.56 | 21.36 |
| M Xylene (wt%) | 56.08 | 46.36 | 44.88 | 48.48 | 48.45 |
| O Xylene (wt %) | 25.55 | 19.56 | 18.17 | 21.48 | 21.40 |
| C9+ Arom (wt %) | 1.26 | 6.53 | 8.11 | 3.04 | 2.60 |
| % P Xylene made | | 6.96 | 7.22 | 8.67 | 9.47 |
| % Xylenes lost | | 9.36 | 12.14 | 3.21 | 2.47 |
| % E Benzene lost | | 30.05 | 36.79 | 11.21 | 8.81 |

TABLE 17

Methylation of Toluene

| Time (hr) | 5 | 18 | 26 |
|---|---|---|---|
| Feed Rate (ml/hr) | 5.0 | 5.0 | 1.5 |
| Gas (wt %) | 1.09 | 1.42 | 0.61 |
| Benzene (wt %) | 0.24 | 0.20 | 0.33 |
| Toluene (wt %) | 80.19 | 84.66 | 74.84 |
| P Xylene (wt %) | 3.65 | 2.83 | 4.38 |
| M Xylene (wt %) | 3.60 | 2.63 | 4.85 |
| O Xylene (wt %) | 7.54 | 6.17 | 9.04 |
| C9+ Arom (wt %) | 3.70 | 2.09 | 5.90 |
| Total Xylenes | 14.79 | 11.63 | 18.27 |
| % Orthoxylene in Xylenes | 50.98 | 53.09 | 49.46 |

TABLE 18

Ethylation of benzene

| | feed | | | | |
|---|---|---|---|---|---|
| Time (hr) | | 2 | 3 | 6 | 10 |
| Temperature (°C.) | | 350 | 330 | 300 | 280 |
| Gas (wt %) | 10.69 | 0.26 | 0.21 | 0.57 | 5.37 |
| Benzene (wt %) | 89.31 | 66.44 | 65.90 | 64.14 | 75.16 |
| Toluene (wt %) | | 0.23 | 0.19 | 0.15 | 0.18 |
| Ethylbenzene (wt %) | | 28.48 | 29.30 | 29.26 | 17.34 |
| Diethylbenzene (wt %) | | 4.48 | 4.32 | 5.74 | 1.96 |
| Benzene conv (wt %) | | 25.61 | 26.11 | 28.18 | 15.84 |
| Selectivity to EB | | 85.52 | 86.46 | 82.92 | 89.06 |

TABLE 19

Hydroisomerisation of xylenes

| | feed | | | | |
|---|---|---|---|---|---|
| Time (hr) | | 5 | 36 | 72 | 96 |
| Temperature (°C.) | | 330 | 370 | 400 | 430 |
| Feed Rates: | | | | | |
| Xylenes (ml/h) | | 5.70 | 5.70 | 5.70 | 11.40 |
| Hydrogen (l/h) | | 4.52 | 4.52 | 4.52 | 4.52 |
| Gas (wt %) | | 0.14 | 0.11 | 0.12 | 0.13 |
| Benzene (wt %) | 0.66 | 1.11 | 0.90 | 0.90 | 0.91 |
| Toluene (wt %) | 2.92 | 6.26 | 4.85 | 4.49 | 4.08 |
| Non Arom (wt %) | 0.49 | 1.06 | 1.06 | 1.11 | 1.15 |
| E Benzene (wt %) | 17.46 | 13.11 | 14.72 | 15.04 | 15.39 |
| P Xylene (wt %) | 7.52 | 14.82 | 16.36 | 17.02 | 17.17 |
| M Xylene (wt %) | 47.99 | 37.41 | 38.37 | 38.58 | 38.64 |
| O Xylene (wt %) | 21.51 | 17.12 | 17.65 | 17.51 | 17.93 |
| C9+ Arom (wt %) | 1.45 | 8.97 | 6.00 | 5.23 | 4.60 |
| % P Xylene made | | 7.30 | 8.84 | 9.50 | 9.65 |
| % Xylenes lost | | 9.96 | 6.03 | 5.08 | 4.26 |

TABLE 19-continued

Hydroisomerisation of xylenes

| | feed | | | | |
|---|---|---|---|---|---|
| % E Benzene lost | | 24.92 | 15.68 | 13.87 | 11.84 |

We claim:

1. A catalyst comprising zeolite NU-85 having a composition expressed on an anhydrous basis, in terms of mole ratios of oxide, by the formula:

100 $XO_2$: less than or equal to 10 $Y_2O_3$: less than or equal to 20 $R_{2/n}O$ where R is one or more cations of valency n, X is silicon and/or germanium, Y is one or more of aluminum, iron, gallium, boron, titanium, vanadium, zirconium, molybdenum, arsenic, antimony, chromium and manganese and having, in its as-prepared form, lattice images which, when orientated to show the 20±0.2 Angstrom fringes of zeolite EU-1 exhibit intergrown 12.5±0.2 Angstrom fringes together with said 20±0.2 Angstrom fringes and/or a X-ray diffraction pattern including the lines shown in Table 1 in which R is at least partially hydrogen.

2. A catalyst as claimed in claim 1 in which the hydrogen is partially or completely replaced by a metal.

3. A catalyst comprising zeolite NU-85, having a composition expressed on an anhydrous basis, in terms of mole ratios of oxide, by the formula:

100 $XO_2$: less than or equal to 10 $Y_2O_3$: less than or equal to 20 $R_{2/n}O$ where R is one or more cations of valency n, X is silicon and/or germanium, Y is one or more of aluminum, iron, gallium, boron, titanium, vanadium, zirconium, molybdenum, arsenic, antimony, chromium and manganese and having, in its as-prepared form, lattice images which, when orientated to show the 20 ±0.2 Angstrom fringes of zeolite EU-1 exhibit intergrown 12.5 ±0.2 Angstrom fringes together with said 20 ±0.2 Angstrom fringes and/or a X-ray diffraction pattern including the lines shown in Table 1 in which R is other than hydrogen.

4. A catalyst as claimed in any one of claims 1 to 3 further comprising a component selected from (a) a binder;

(b) a catalyst support material;

(c) a further zeolite or a molecular sieve;

(d) a metal; and (e) a further catalyst or a combination thereof.

* * * * *